United States Patent
Maloisel et al.

(10) Patent No.: US 11,718,643 B2
(45) Date of Patent: *Aug. 8, 2023

(54) MULTIMODAL ANION EXCHANGE MATRICES

(71) Applicant: GE HEALTHCARE BIOPROCESS R&D AB, Uppsala (SE)

(72) Inventors: Jean-Luc Maloisel, Uppsala (SE); Gustav Rodrigo, Uppsala (SE); Bjorn Noren, Uppsala (SE); Virendra Kumbhar, Gurgaon (IN)

(73) Assignee: Cytiva BioProcess R&D AB, Uppsala (SE)

( * ) Notice: Subject to any disclaimer, the term of this patent is extended or adjusted under 35 U.S.C. 154(b) by 273 days.

This patent is subject to a terminal disclaimer.

(21) Appl. No.: 14/441,129

(22) PCT Filed: Nov. 11, 2013

(86) PCT No.: PCT/SE2013/051325
§ 371 (c)(1),
(2) Date: May 6, 2015

(87) PCT Pub. No.: WO2014/077762
PCT Pub. Date: May 22, 2014

(65) Prior Publication Data
US 2015/0299248 A1   Oct. 22, 2015

(30) Foreign Application Priority Data
Nov. 13, 2012   (SE) .................................. 1251286-9

(51) Int. Cl.
*B01D 15/32* (2006.01)
*B01D 15/36* (2006.01)
(Continued)

(52) U.S. Cl.
CPC ............ *C07K 1/165* (2013.01); *B01D 15/327* (2013.01); *B01D 15/363* (2013.01);
(Continued)

(58) Field of Classification Search
CPC .......... C07K 1/165; C07K 1/36; C07K 1/152; C07K 16/00; C07K 16/065; B01J 20/265;
(Continued)

(56) References Cited

U.S. PATENT DOCUMENTS 4,043,997 A    8/1977 Schroeder
4,675,384 A *  6/1987 Dromard .............. C07K 14/765
                                                       210/263
(Continued)

FOREIGN PATENT DOCUMENTS

EP    1718386 A1    11/2006
EP    2919902 A1     9/2015
(Continued)

OTHER PUBLICATIONS

Molinspiration, "Calculation of molecular properties and bioactivity score", Molinspiration Cheminformatics 2017. Retrieved from http://www.molinspiration.com/cgi-bin/properties. Accessed Sep. 14, 2017.*
(Continued)

*Primary Examiner* — Benjamin L Lebron
(74) *Attorney, Agent, or Firm* — Eversheds Sutherland (US) LLP

(57) ABSTRACT

The invention discloses a separation matrix which comprises a plurality of separation ligands, defined by the formula $R_1$-$L_1$-N($R_3$)-$L_2$-R, immobilized on a support, wherein $R_1$ is a five- or six-membered, substituted or non-substituted ring structure or a hydroxyethyl or hydroxypropyl group; $L_1$ is either a methylene group or a covalent bond; $R_2$ is a five- or six-membered, substituted or non-substituted ring structure; $L_2$ is either a methylene group or a covalent bond; $R_3$ is a
(Continued)

methyl group; and wherein if $R_1$ is a hydroxyethyl group and $L_1$ is a covalent bond, $R_2$ is a substituted aromatic ring structure or a substituted or non-substituted aliphatic ring structure.

15 Claims, 6 Drawing Sheets

(51) Int. Cl.

| | | |
|---|---|---|
| *B01D 15/38* | (2006.01) | |
| *B01J 20/26* | (2006.01) | |
| *B01J 20/28* | (2006.01) | |
| *B01J 20/286* | (2006.01) | |
| *B01J 20/289* | (2006.01) | |
| *B01J 20/32* | (2006.01) | |
| *B01J 41/20* | (2006.01) | |
| *C07K 1/16* | (2006.01) | |
| *C07K 1/36* | (2006.01) | |
| *C07K 16/00* | (2006.01) | |
| *C07K 16/06* | (2006.01) | |
| *G01N 33/544* | (2006.01) | |

(52) U.S. Cl.
CPC ........ *B01D 15/3847* (2013.01); *B01J 20/265* (2013.01); *B01J 20/286* (2013.01); *B01J 20/289* (2013.01); *B01J 20/28016* (2013.01); *B01J 20/3204* (2013.01); *B01J 20/3208* (2013.01); *B01J 20/3219* (2013.01); *B01J 20/3251* (2013.01); *B01J 20/3253* (2013.01); *B01J 20/3255* (2013.01); *B01J 20/3285* (2013.01); *B01J 41/20* (2013.01); *C07K 1/36* (2013.01); *C07K 16/00* (2013.01); *C07K 16/065* (2013.01); *G01N 33/544* (2013.01); *B01D 15/3809* (2013.01); *B01D 15/3885* (2013.01); *B01J 2220/52* (2013.01); *B01J 2220/80* (2013.01)

(58) Field of Classification Search
CPC .. B01J 41/20; B01J 2220/80; B01J 20/28016; B01J 20/286; B01J 20/289; B01J 20/3204; B01J 20/3208; B01J 20/3219; B01J 20/3251; B01J 20/3253; B01J 20/3255; B01J 2220/52; G01N 33/544; B01D 15/327; B01D 15/363; B01D 15/3809; B01D 15/3847; B01D 15/3885
See application file for complete search history.

(56) References Cited

U.S. PATENT DOCUMENTS

| | | |
|---|---|---|
| 6,428,707 B1 | 8/2002 | Berg et al. |
| 6,602,990 B1 | 8/2003 | Berg |
| 7,385,040 B2 | 6/2008 | Johansson et al. |
| 2008/0116138 A1 | 5/2008 | Kondo et al. |
| 2008/0132683 A1 | 6/2008 | Lihme et al. |
| 2008/0311681 A1* | 12/2008 | Johannsen ............... B01J 20/22 436/548 |
| 2009/0275141 A1 | 11/2009 | Betley et al. |
| 2011/0118442 A1 | 5/2011 | Engstrand et al. |
| 2011/0139717 A1 | 6/2011 | Malenfant et al. |

FOREIGN PATENT DOCUMENTS

| | | |
|---|---|---|
| GB | 2221466 A | 2/1990 |
| JP | 52-144699 A | 12/1977 |
| JP | 2008-518885 A | 6/2008 |
| WO | 2005/082483 A1 | 9/2005 |
| WO | 2006/043896 A1 | 4/2006 |
| WO | 2006/086705 | 8/2006 |
| WO | 2014/077762 A1 | 5/2014 |

OTHER PUBLICATIONS

EP Search Report issued in corresponding EP Appln. No. 13854329.3 national phase of PCT/SE2013/051325 (dated Nov. 11, 2015).
Hermanson et al., Immobilized Affinity Ligand Techniques, Academic Press, Inc., 12 pp (1992).
Hagel et al. Apparent pore size distributions of chromatography media, J. Chromatograpy A, 743:33-42 (1996).
Hjerten, Stellan, The Preparation of Agarose Spheres for Chromatography of Molecules and Particles, Biochim. Biophys. Acta, 79:393-398 (1964).
Arshady, Reza, Styrene Based Polymer Supports Developed by Suspension Polymerization, LA Chimica E L'Industria, 70(9):70-75 (1988).
Sangster, James, Octanol-Water Partition Coefficients of Simple Organic Compounds, J. Phys. Chem. Ref. Data, 18(3):1111-1117 (1989).
International Search Report and Written Opinion Received for PCT Application No. PCT/SE2013/051325, dated Feb. 21, 2014, 6 Pages.
International Preliminary Report on Patentability Received for PCT Application No. PCT/SE2013/051325, dated May 19, 2015, 8 Pages.
Office Action Received received for Japanese Patent Application No. 2015-541741, dated Jul. 4, 2017, 4 pages (1 Page English Translation + 3 Pages of Official Copy).
Office Action for European Patent Appl. No. 13 854 329.3, filed Nov. 11, 2013, 6 pages, dated Aug. 29, 2018.
Anonymous: "Sodium triacetoxyborohydride—Wikipedia", Aug. 16, 2012, XP055498787, Retrieved from the Internet: URL: https://en.wikipedia.org/w/index.php? title=Sodium_triacetoxyborohydride&oldid=507619669 [retrieved on Aug. 9, 2018].

* cited by examiner

MULTIMODAL ANION EXCHANGE MATRICES

TECHNICAL FIELD OF THE INVENTION

The present invention relates to separation matrices with novel ligands, which can be used for the purification of biomolecules such as proteins. The present matrices are useful e.g. for the purification of antibodies. Consequently, the invention also encompasses use of the chromatography matrix for separation, a method of separating antibodies from other compounds with the chromatography matrix and a method of synthesizing the separation ligands.

BACKGROUND OF THE INVENTION

The clinical success of monoclonal antibodies (MAbs) is one of the most exciting achievements in the biopharmaceutical industry, resulting in annual production requirements of, in some cases, several tonnes—joining insulin and plasma proteins in sheer scale of bulk production. MAbs are currently the second largest category of biotech drugs on the market after growth factors, but are by far the fastest growing category and are believed by many to be the future of the biotechnology industry. To meet this demand, cell culture capacity is increasing with reactors of up to 25 000 l. In addition, expression levels, currently in the range of 3 to 5 g/l, are expected to further increase, which will put additional demand on the development of purification tools such as high-throughput media and process solutions. Key concerns in large-scale purification (downstream processing) differ from those typical at laboratory scale; the emphasis in large-scale purification is developing robust and cost effective protocols and decreasing the number of unit operations in order to improve overall process economy. Current trends in antibody production show that affinity chromatography using Protein A media is the most cost effective alternative for capture of antibodies.

Common contaminants remaining after a protein A capture step are antibody aggregates, leached protein A, DNA and host cell proteins. These and any adventitious virus particles must be removed in further purification steps, e.g. one or more chromatography steps. Anion exchange, cation exchange and hydrophobic interaction chromatography steps have all been used for this purpose, either in flow-through or bind-elute mode. More recently, multimodal ion exchange matrices have been shown to give efficient clearance of these contaminants. In particular, the multimodal anion exchange matrices described in WO 2006/043896 (A1) are useful for removal of aggregates, host cell proteins and other contaminants e.g. in flow-through mode where the contaminants bind to the matrix and the antibody is recovered in the flow-through and optionally in a wash buffer. Such matrices with the ligand N-methyl, N-benzyl ethanolamine are commercially available as Capto™ adhere and Capto ImpRes adhere (GE Healthcare, Sweden).

Due to the large production volumes of MAbs and the high costs associated with Mab-based therapies, there is a considerable pressure to increase the production efficiency and throughput in Mab purification. There is also a general need to reduce the amounts of immunogenic and otherwise potentially harmful residual contaminants in Mabs for therapeutic use. This means that any improvement in the clearance of contaminants in a particular step is valuable, both as it can reduce the contaminant level in the product and as it may also enable a purification process with fewer steps, which leads to a major cost reduction.

Accordingly there is a need for new multimodal anion exchange ligands with improved clearance of contaminants such as antibody aggregates, host cell proteins, DNA, leached protein A and DNA from antibodies as well as from similar proteins such as antibody fragments, antibody fusion proteins etc.

SUMMARY OF THE INVENTION

One aspect of the invention is to provide a novel matrix which is useful in the separation of antibodies from other components of a liquid. This is achieved with a matrix as defined in claim 1.

One advantage is that efficient separations can be achieved also at high ionic strengths. Further advantages are that the antibody yield and the clearance of impurities are improved.

A second aspect of the invention is the use of the novel matrix in separation of biomolecules. This is achieved by the methods as defined in the claims.

A third aspect of the invention is a method of separating antibodies from other solutes. This is achieved with a method as defined in the claims.

A fourth aspect of the invention is to provide a method of synthesizing separation ligands which are suitable for preparation of matrices to be used in antibody separations. This is achieved by the method as defined in the claims.

Further suitable embodiments of the invention are described in the dependent claims.

DEFINITIONS

Figure 1:
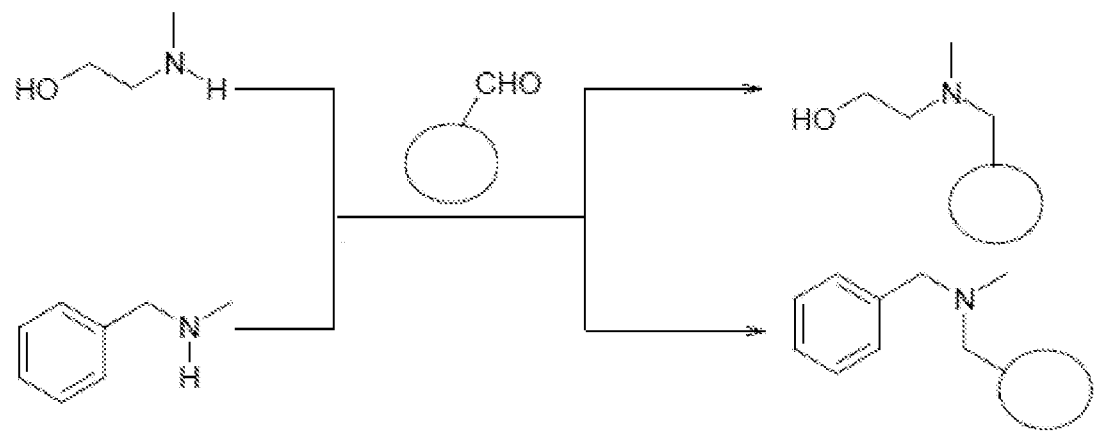
FIG. 1. Synthesis of tertiary amine ligands by reductive amination according to one aspect of the invention.

The terms "antibody" and "immunoglobulin" are used interchangeably in the present specification.

The term "separation matrix" is used herein to denote a material comprised of a support to which one or more ligands comprising functional groups have been coupled. The term "resin" is sometimes used for a separation matrix in this field.

The term "multi-modal" separation matrix refers to a matrix capable of providing at least two different, but co-operative, sites which interact with the compound to be bound. For example, one of these sites may give an attractive type of charge-charge interaction between the ligand and the substance of interest. The other site may give electron acceptor-donor interaction and/or hydrophobic and/or hydrophilic interactions. Electron donor-acceptor interactions include interactions such as hydrogen-bonding, π-π, cation-π, charge transfer, dipole-dipole, induced dipole etc. "Multi-modal" separation matrices are also known as "mixed mode" separation matrices.

The term "surface" means herein all external surfaces, and includes in the case of a porous support outer surfaces as well as pore surfaces.

The term "eluent" is used in its conventional meaning in this field, i.e. a buffer of suitable pH and/or ionic strength to release one or more compounds from a separation matrix.

The term "capture step" refers in the context of liquid chromatography to the initial step of a separation procedure. Most commonly, a capture step includes clarification, concentration, stabilisation and a significant purification from soluble impurities. After the capture step, an intermediate purification may follow, which further reduces remaining amounts of impurities such as host cell proteins, DNA, viruses, endotoxins, nutrients, components of a cell culture medium, such as antifoam agents and antibiotics, and product-related impurities, such as aggregates, misfolded species and aggregates.

The term "disposable" means herein in the context of chromatography columns and other separation matrices a matrix which is intended for single use, or a limited number of uses. Disposable products are advantageously used to remove contaminants which are harmful even in very small amounts, in which case it is convenient to adsorb said contaminant to the matrix and then discard the matrix. Another situation when disposable products are desired is for sterile processing, in which case the matrix is sterile or at least aseptic.

The term "polishing step" refers in the context of liquid chromatography to a final purification step, wherein trace impurities are removed to leave an active, safe product. Impurities removed during the polishing step are often conformers of the target molecule or suspected leakage products.

The term an "Fc-binding protein" means a protein capable of binding to the crystallisable part (Fc) of an antibody and includes e.g. Protein A and Protein G, or any fragment or fusion protein thereof that has maintained said binding property.

DETAILED DESCRIPTION OF EMBODIMENTS

In one aspect the present invention discloses a separation matrix comprising a plurality of separation ligands. The separation ligands are defined by formula (I).

$R_1$-$L_1$-$N(R_3)$-$L_2$-$R_2$ (I)

$R_1$ is here a hydroxyethyl or a hydroxypropyl group or a five- or six-membered, substituted or non-substituted ring structure;

$L_1$ is either a methylene group or a covalent bond;

$R_2$ is a five- or six-membered, substituted or non-substituted ring structure;

$L_2$ is either a methylene group or a covalent bond;

$R_3$ is a methyl group;

If $R_1$ is a hydroxyethyl group and $L_1$ is a covalent bond, then $R_2$ is a substituted aromatic ring structure or a substituted or non-substituted aliphatic ring structure.

As shown by formula (I), the ligand is a tertiary amine with a nucleophilic amine nitrogen, suitable for coupling to e.g. electrophilic groups on a support. After such coupling, the nitrogen becomes a quaternary ammonium group, which allows for ionic interactions with proteins over a broad pH interval. The $R_1$, $R_2$ and $R_3$ groups provide for a suitable level of additional interactions with proteins by hydrophobic interactions, hydrogen bonding, π-electron interactions etc. In addition, the steric arrangement of the $R_1$, $R_2$ and $R_3$ groups around the nitrogen can modulate the total interaction strength with proteins and the balance between the ionic interactions and the additional interactions. When either or both of R1 and R2 is a substituted ring structure, all the substituents on the ring(s) can suitably be one- or two-carbon groups, such as e.g. methyl groups, methoxy groups, trifluoromethyl groups, ethyl groups and/or hydroxyethyl groups. The ligands can suitably have a low molecular weight, such as below 350 Da or within the interval 150-350 Da, which prevents overly strong binding to proteins. Each ligand can suitably comprise a single nitrogen, which is advantageous in that it enables the modulation of the interactions strength as described above and in that it enables a well-defined coupling site.

Consequently, as immobilized, the ligand according to the invention is considered to be a multi-modal anion exchange ligand, since in addition to the positively charged quaternary ammonium group it also comprises the ring structure which is hydrophobic. Methods for immobilisation of ligands to porous or non-porous surfaces are well known in this field; see e.g. Immobilized Affinity Ligand Techniques, Hermanson et al, Greg T. Hermanson, A. Krishna Mallia and Paul K. Smith, Academic Press, INC, 1992. In certain embodiments, the ligand content per ml matrix is in a range close to what is commonly used for conventional ion-exchange matrices. It can e.g. be 10-200 μmol/ml, such as 20-150 or 25-100 μmol/ml.

In some embodiments the separation ligands are immobilized via the amine group. As outlined above, this results in the conversion of the amine to a quaternary ammonium group, which is positively charged over the entire pH range used for protein separations. The immobilization can suitably be made by introducing electrophilic groups on the support. This can e.g. be done by activation of hydroxyl groups on polysaccharides or other hydroxyfunctional supports. Several activation reagents can be used for this purpose, e.g. epichlorohydrin, bis-epoxy compounds, allyl glycidyl ether, tosyl chloride, tresyl chloride etc. according to methods well known in the art.

In some embodiments, the ligands in free form (i.e. the tertiary amines before coupling to the support) have an octanol-water distribution coefficient (lg P) of 1.8 or higher, such as 1.8-5, 1.8-4, 2-4, 1.8-3 or 2-3. The value of P is defined as $P=[X]^{org}/[X]^{aq}$ in an octanol-water two phase system, where $[X]^{org}$ is the equilibrium concentration of substance X in the octanol phase and $[X]^{aq}$ is the equilibrium concentration in the water phase. The data are determined at room temperature (about 25° C.) with n-octanol. Lg P values are commonly used in both pharmaceutical and environmental sciences to assess the relative hydrophobicity of different compounds. Methods of measuring lg P include shake-flask methods and column methods as described e.g. in J Sangster: J Phys Chem Ref Data 18(3), 1111-1227 (1989). Lg P can also be estimated by computer softwares, e.g. ACD/Labs LogP DB (Advanced Chemistry Development Inc), from structure formulas of organic compounds.

As outlined in the Examples, the ability of matrices with immobilized ligands according to the invention to discriminate between antibodies and aggregates or host cell proteins is higher when lg P is at least 1.8 and the best discrimination is obtained for ligands with lg P 1.8-3.

In some embodiments, $R_2$ is a substituted or non-substituted phenyl or cyclohexyl ring structure. The six-membered aromatic or aliphatic ring structure is compact and provides hydrophobicity without excessive steric hindrance.

In certain embodiments, $R_2$ comprises one or more methyl, methoxy or trifluorocarbon substituents on the ring structure. These substituents can further increase the hydrophobicity which is useful in particular situations.

In some embodiments, $R_2$ is a phenyl ring comprising a substituent, such as a single trifluorocarbon substituent, in the para position. Trifluorocarbon provides hydrophobicity but is a rather bulky substituent and it is advantageous if it is used in the para position.

In certain embodiments, $R_1$ is a hydroxyethyl group and $L_1$ is a covalent bond. The hydroxyethyl group can provide additional interactions through hydrogen bonding with proteins and will also balance the total hydrophobicity of the ligand. As described above, the ring structure $R_2$ is then either a substituted aromatic ring or an aliphatic ring structure, both of which can provide better selectivity in antibody purification than an unsubstituted aromatic ring.

In some embodiments, $R_1$ is a substituted or non-substituted five- or six-membered ring structure. The ring structure can e.g. be aromatic or non-aromatic and may be either an all-carbon ring or it may incorporate one or more heteroatoms such as sulfur, oxygen or nitrogen in the ring. In the case when each ligand comprises a single nitrogen, the heteroatom(s) will not be nitrogen. In these embodiments the ligand contains two ring structures, which is advantageous in certain applications. If both $R_1$ and $R_2$ are aromatic ring structures, it may be speculated that they are able to interact with the quaternary ammonium group via cation—π-electron interactions. This may modulate the charge interactions with negative counterions and with negative charges on the target biomolecules in an advantageous way. In certain embodiments $R_1$ is a substituted or non-substituted phenyl or thiophene ring.

In some embodiments $L_1$ is a methylene group —$CH_2$—. When $R_1$ is a ring structure, the presence of a methylene group increases the mobility of the ring and if the ring is aromatic, the methylene group can also affect the electron structure of the nitrogen in a favourable way.

In certain embodiments the ligands are defined by formula (II), (III), (IV) or (V)

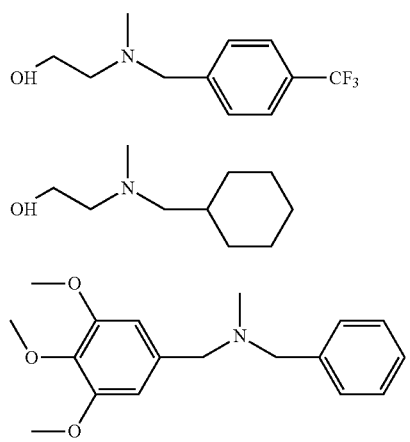

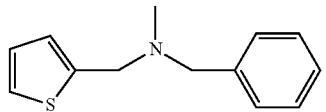

The support may be made from an organic or inorganic material, and may be porous or non-porous. In one embodiment, the support is prepared from a native polymer, such as cross-linked carbohydrate material, e.g. agarose, agar, cellulose, dextran, chitosan, konjac, carrageenan, gellan, alginate, pectin, starch, etc. The native polymer supports are easily prepared and optionally cross-linked according to standard methods, such as inverse suspension gelation (S Hjertén: Biochim Biophys Acta 79(2), 393-398 (1964). In an especially advantageous embodiment, the support is a kind of relatively rigid but porous agarose, which is prepared by a method that enhances its flow properties, see e.g. U.S. Pat. No. 6,602,990 (Berg) or SE 0402322-2 (Berg et al.). In an alternative embodiment, the support is prepared from a synthetic polymer or copolymer, such as cross-linked synthetic polymers, e.g. styrene or styrene derivatives, divinylbenzene, acrylamides, acrylate esters, methacrylate esters, vinyl esters, vinyl amides etc. Such synthetic polymers are easily prepared and optionally cross-linked according to standard methods, see e.g. "Styrene based polymer supports developed by suspension polymerization" (R Arshady: Chimica e L'Industria 70(9), 70-75 (1988)). Native or synthetic polymer supports are also available from commercial sources, such as GE Healthcare, Uppsala, Sweden, for example in the form of porous particles. In yet an alternative embodiment, the support is prepared from an inorganic polymer, such as silica. Inorganic porous and non-porous supports are well known in this field and easily prepared according to standard methods. The support may further comprise a filler material, such as magnetic particles, e.g. magnetite particles dispersed in agarose gels or high density particles, e.g. metal alloy or tungsten carbide particles dispersed in agarose gels. These embodiments are useful for magnetic separations and expanded bed separations respectively.

Suitable particle sizes of the present separation matrix may be in the diameter range of 5-500 μm, such as 10-100 μm, e.g. 20-80 μm. In the case of essentially spherical particles, the average particle size may be in the range of 5-1000 μm, such as 10-500. In a specific embodiment, the average particle size is in the range of 10-200 μm. The skilled person in this field can easily choose the suitable particle size and porosity depending on the process to be used. For example, for a large scale process, for economical reasons, a more porous but rigid support may be preferred to allow processing of large volumes, especially for the capture step. In chromatography, process parameters such as the size and the shape of the column will affect the choice.

In certain embodiments the support is porous. The pore size can be in a range suitable to accommodate and allow rapid mass transport of biomacromolecules such as proteins. Typically, at least 25%, such as at least 50% of the pore volume can be accessible to macromolecules having a hydrodynamic diameter of at least about 12.5 nm, as exemplified by the protein thyroglobulin or by dextran of molecular weight 110 kDa. Supports with such porosities can be e.g. agarose gels of max 6% or max 4% agarose concentration, or the high rigidity crosslinked agarose supports described in U.S. Pat. No. 6,602,990. Methods for measuring the accessible pore volume fraction, $K_D$, are described in e.g. L Hagel et al: J Chromatogr A 743, 33-42 (1996).

In some embodiments the matrix is in the form of particles with a non-homogeneous structure. Particles can have the ligand immobilized predominantly, or only, on a core portion of each particle, with lower ligand content, or no ligands, in an outer shell of each particle, surrounding the core portion. Such particles may e.g. constitute at least 90% of the matrix and the core portion of these particles may take up at least 50%, such as at least 90% of the particle volume, while the outer shell may take up less than 50%, such as less than 10% of the particle volume. The shell may have the same pore structure as the core, but it may also have a lower average pore size, such as at least 10% lower average pore diameter, than the core. Such particles are useful in that species larger than the pores of the shell will not penetrate into the core and bind to the ligands. This introduces a further element of size selectivity into the separation. Other non-homogeneous particle types contemplated include pellicular particles with the ligands predominantly in a porous shell on a solid core, or particles with various forms of radial ligand concentration and/or pore size gradients.

Figure 7:
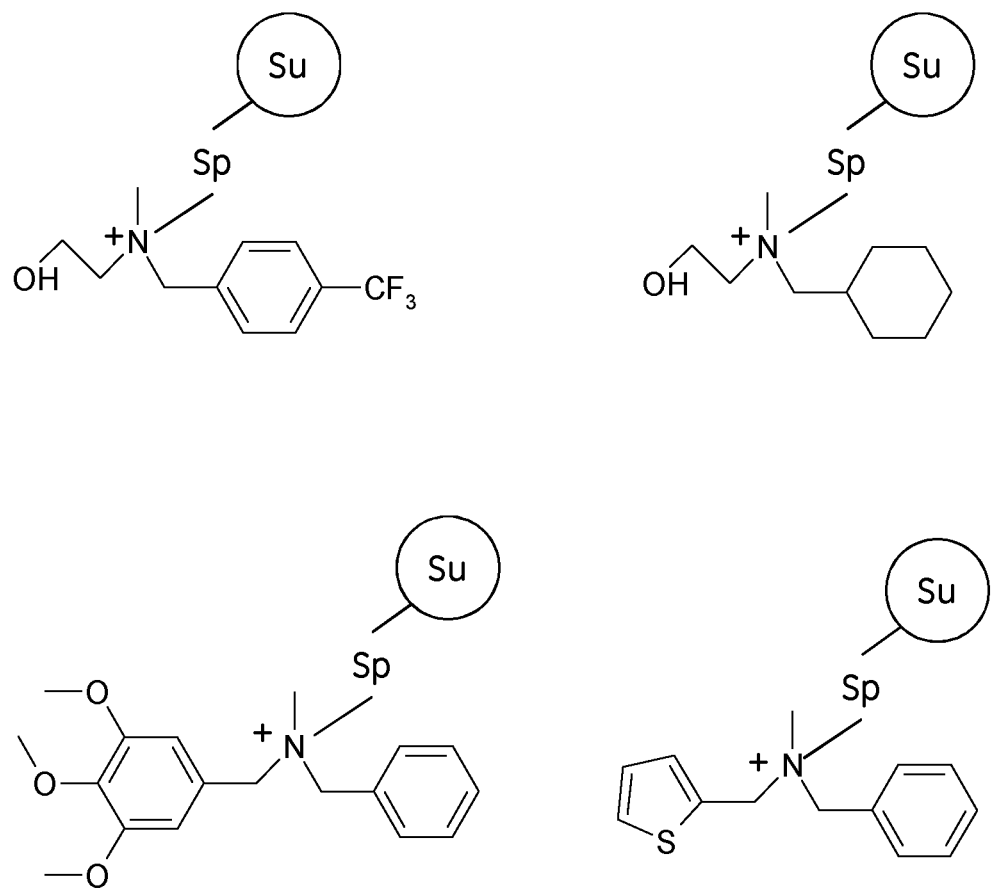
FIG. 7. Structure of four matrices according to the invention, with ligands coupled via a spacer.

In certain embodiments the immobilized separation ligands are immobilized on the support Su via a spacer Sp, as defined in formula (VI) and exemplified in FIG. 7.

(VI)

In some embodiments the spacer Sp comprises a chain of 2-8 carbon atoms, optionally interrupted by and/or ending in one or more ether groups and optionally substituted by one or more hydroxyl groups. The coupling may be carried out following any conventional covalent coupling methodology such as by use of epichlorohydrin; epibromohydrin; allyl-glycidylether; bis-epoxides such as butanedioldiglycidylether; halogen-substituted aliphatic substances such as dichloro-propanol, where the activation/coupling reagent forms the spacer.

In a specific embodiment, the ligand according to the invention is coupled to the support via a longer spacer molecule, also known as extender. Extenders are well known in this field, and commonly used to increase sterically the distance between ligand and support. Extenders are sometimes denoted tentacles or flexible arms, for a more detailed description of possible chemical structures, see e.g. U.S. Pat. No. 6,428,707, which is hereby included herein via reference. In brief, the extender may be in the form of a polymer such as a homo- or a copolymer. Hydrophilic polymeric extenders may be of synthetic origin, i.e. with a synthetic skeleton, or of biological origin, i.e. a biopolymer with a naturally occurring skeleton. Typical synthetic polymers are polyvinyl alcohols, polyacryl- and polymethacrylamides, polyvinyl ethers etc. Typical biopolymers are polysaccharides, such as starch, cellulose, dextran, agarose.

In certain embodiments the support comprises particles, such as porous particles. The particles can be essentially spherical, elongated or irregularly formed particles. In a specific embodiment, the separation matrix is dried, such as dried particles which upon use are soaked in liquid to retain their original form. In an illustrative embodiment, such a dried separation matrix is comprised of dried agarose particles. However, the matrix according to the invention may alternatively take any other shape conventionally used in separation, such as monoliths; filters or membranes; capillaries; chips; surfaces; etc. The support may also be in the form of nanoparticles or even ligand-polymer conjugates, which can be separated from a liquid by ultrafiltration, precipitation or the formation of aqueous two-phase systems.

In some embodiments the support comprises a porous membrane. The membrane can e.g. be in the form of a single membrane sheet, a hollow fibre, a stack of sheets, a roll or a bundle of hollow fibres. The membrane can suitably be a microfiltration membrane, e.g. with an average pore size in the 0.1 µm to 10 µm range, such as in the 1-5 µm range. It can be a cellulosic membrane, such as a cross-linked cellulose membrane.

In a second aspect the invention discloses use of a separation matrix as described above in biomolecule separation, such as protein separation. In a first embodiment, the present invention uses a separation matrix as described above in protein separation. In an advantageous embodiment of the present use, the protein is an antibody; an antibody fragment; or a fusion protein comprising an antibody. In another embodiment, the present invention uses a separation matrix as described above in the separation of any other compound, e.g. one selected from the group consisting of polypeptides; nucleic acids, e.g. DNA, RNA or oligonucleotides thereof, plasmids; virus; prions; cells, such as prokaryotic or eukaryotic cells; lipids; carbohydrates; organic molecules, such as small organic molecules; drug targets; diagnostic marker molecules. The use will be discussed in more detail below. As the skilled person in this field will realise, in the present application, the term separation is used for purification; isolation; and removal of compounds, but it also encompasses identification of a target compound such as for diagnostic purposes.

In a third aspect the invention discloses a method of separating one or more antibodies from one or more other compounds in a liquid sample, wherein a mobile phase comprising said antibodies and compound(s) is contacted with a separation matrix as described above. In an advantageous embodiment, the present method is carried out using the principles of liquid chromatography, i.e. by passing a mobile phase over a chromatography column comprising the separation matrix according to the invention. In another alternative embodiment, the present method is carried out using a batch-wise chromatography process, wherein the separation matrix is added to a vessel comprising the liquid sample. In a specific embodiment, the separation matrix added in batch-wise mode comprises dried particles, such as dried agarose particles. In another embodiment, the method is carried out using the principles of expanded bed chromatography i.e. by adding the mobile phase to an expanded bed, such as a fluidised bed, of a separation matrix which is in the form of essentially spherical particles comprising high density filler. The method can also be carried out by magnetic separation, where the separation matrix is in the form of particles comprising magnetic filler.

In a first embodiment of the present method, undesired compounds are adsorbed to the separation matrix while the desired compound, such as the antibodies, remains in the mobile phase without being adsorbed. As understood by the skilled person in this field, the nature and identity of the adsorbed compounds will depend on the origin of the liquid sample. Examples of compounds adsorbed in the embodiment where desired antibodies are not adsorbed are cells and cell debris; proteins and peptides; nucleic acids, such as DNA and RNA; endotoxins, viruses, residues from the culture media etc. In a specific embodiment, the present separation matrix is provided in a chromatography column and the mobile phase is passed across said column by gravity and/or pumping, the antibodies being recovered in the flow-through of the column. Thus, an advantage of this embodiment is that it does not require any elution of the antibody product from the column. Avoiding a specific elution step is attractive from a process point of view, since fewer steps will result in a more rapid purification protocol and consequently reduce the process costs. In addition antibodies are sensitive to certain conditions that would e.g. cause aggregation, impair their folding pattern; or degrade them by attacking their peptide bonds. Thus, even though elution conditions for anion-exchangers in general do not involve any extreme chemicals, the change of salt and/or pH may affect the sensitive antibody, the effect varying from species to species depending on the pI, charge distribution etc. Consequently, another advantage of this embodiment is that it avoids adding an eluent and applying eluting conditions to the desired compounds. To obtain the most suitable conditions for adsorption of compounds, the liquid sample is combined with a suitable buffer or other liquid to provide a mobile phase. The present embodiment can be run under conditions conventional for anion-exchange chromatography, which commonly involves adsorption at a relatively low salt concentration. Thus, in one embodiment of the present method, the conductivity of the mobile phase is in the range of 0-25, such as 10-15 mS/cm. In an alternative embodiment the salt concentration can be above what is normally used in ion exchange chromatography. The conductivity of the mobile phase can then be at least 10 mS/cm, e.g. in the range of 10-50, such as 10-30, 15-30 or 20-30 mS/cm. In one embodiment, the pH of the mobile phase is about 4-9, such as 4-7, 5-7, 5-6 or 6-7. If it is desired to subsequently release the adsorbed compounds, e.g. for re-use of the matrix, elution may be carried out at a higher salt concentration, e.g. by use of an increasing salt gradient. The pH value may also or alternatively be shifted, e.g. be a decreasing pH gradient, to elute adsorbed compounds.

In a second and alternative embodiment of the present method, the desired compounds are adsorbed to the matrix as in conventional liquid chromatography. That is to say, the separation matrix is provided in a chromatography column and the mobile phase is passed through the column by gravity and/or pumping and at least part of the antibodies adsorb to the column. In a further step an elution buffer is then passed through the column and antibodies are recovered in the elution buffer after passage of the column. The matrix may then be reused after selective elution of the product. Elution is easily performed by passing an appropriate buffer over the column, where the buffer may e.g. have a salt content and/or a pH causing desorption of the desired compounds from the matrix. The buffer may also comprise displacers or hydrogen bond breakers (e.g. urea) to induce desorption. If required, one or more washing steps may be applied before or between any such passage(s). In one embodiment, the operating conditions of this embodiment are as in conventional ion exchange, i.e. adsorption using a mobile phase having low conductivity and elution by using a high conductivity buffer, as discussed above. The skilled person in this field can easily tune the conditions by testing different conditions and analyse the adsorbed compound(s) and flow-through. In a specific embodiment, the desired compounds are antibodies.

Choosing between the first and the second embodiment above, the skilled person in this field can easily adapt the conditions to adsorb a specific compound, advantageously by control of the pH and/or conductivity. For example, in the separation of antibodies, different classes of antibodies have different charges and charge distribution patterns, which together with the purpose of the separation will decide if it is more preferable to adsorb the antibodies or to let them pass the column without being adsorbed.

The separation can also be performed by batch adsorption. In some embodiments a suspension of matrix particles is contacted with the mobile phase in step b). In a further step c) the matrix particles and the mobile phase are then separated from each other by sedimentation, centrifugation or under the influence of a magnetic field (if the matrix particles are magnetic). In one embodiment undesired compounds bind to the matrix and the antibodies can then be recovered in the separated mobile phase in a further step d). In other embodiments the antibodies bind to the matrix and can be recovered by mixing the separated matrix particles with an elution buffer.

The antibodies separated according to one embodiment of the present invention may originate from any well-known source, such as cells cultured at a surface or from batch-wise or continuous cell culture in tanks, bags or other vessels. Thus, in one embodiment, the liquid is a supernatant obtained from cell culture. Examples of compounds that antibodies need to be separated from are then proteins, DNA, viruses, endotoxins, nutrients, components of a cell culture medium, such as antifoam agents and antibiotics, and product-related impurities, such as misfolded species and aggregates. The step of contact between the mobile phase and the present separation matrix, i.e. the adsorption step, may be preceded by a step of mechanical filtration, centrifugation and/or chromatography. For example, if the liquid sample is a fermentation broth, it is advantageous to mechanically remove cell debris, whole cells and other relatively large components before the step using the present matrix.

In one embodiment, the present method constitutes the capture step of a purification protocol. In a specific embodiment, the liquid sample is a crude feed which is filtrated before contact with the chromatography matrix according to the invention. Consequently, this embodiment would still constitute a capture step, even though the liquid sample has been prepurified by mechanical means. As is well known, the host cells that produce antibodies will also comprise a number of other proteins commonly known as host cell proteins (HCP). Such HCPs include enzymes, such as proteases, and other proteins produced by the host cells. Thus, in one embodiment, substantially all host cell proteins of the liquid sample are removed by the present method, such as by adsorption to the separation matrix.

In alternative embodiments, the present method is used as a second, third or even fourth chromatography step in a cleaning protocol, such as an intermediate purification or polishing step. Thus, in one embodiment, the mobile phase applied to the present separation matrix comprises an antibody-containing eluate from a separation matrix, which can be e.g. an affinity chromatography matrix, an ion exchange matrix, a hydrophobic interaction chromatography matrix or a multimodal matrix. In one embodiment, the liquid sample is an eluate from a preceding affinity chromatography matrix. This affinity chromatography matrix may comprise e.g. peptide or proteinaceous ligands, such as e.g. protein A or varieties thereof, protein G, protein L or single-chain camelide antibody derived ligands. In an advantageous embodiment, the separation matrix from which the eluate is obtained comprises one or more Fc-binding protein ligands, such as Protein A ligands. The term protein A ligands includes in this context native as well as recombinant protein A, or functional fragments thereof. In this context, the term "functional" fragment means a fragment that has retained the original binding properties of the protein. Such affinity matrices are commercially available, such as MabSelect™ or MabSelect SuRe from GE Healthcare. Consequently, in this embodiment, the removed, preferably adsorbed compound may be one or more selected from the group that consists of released proteinaceous ligand; complexes formed between proteinaceous ligand and antibodies, such as proteinaceous ligand-MAb complexes, which complexes may comprise a number of antibodies per proteinaceous ligand molecule, such as 1-4 antibodies complexed with one proteinaceous ligand molecule; and aggregates of released proteinaceous ligand or antibodies. As the skilled person in this field will understand, depending on the specific conditions used in the preceding step, such as affinity chromatography, the eluate may need conditioning by suitable additions or adjustment. Thus, the eluate is combined with a suitable buffer or liquid to provide a mobile phase.

The present method is useful to separate or purify any monoclonal or polyclonal antibody, such as antibodies originating from mammalian or avian hosts, e.g. mice, rodents, primates and humans, or antibodies originating from hybridomas or blood plasma. In one embodiment, the separated antibodies are human or humanised antibodies. The antibodies may be of any class, i.e. selected from the group that consists of IgA, IgD, IgE, IgG, IgY and IgM. In one embodiment, the antibodies are antibodies capable of binding to Protein A, or Fc-containing antibody fragments or fusion proteins. In a specific embodiment, the antibodies are immunoglobulin G (IgG), such as IgG1. In one embodiment, the present method is used to purify antibodies having a pI in the range of 6-9, such as in the range of 7-8. In a specific embodiment, the pI of the purified antibodies is about 9. In the present context, it is to be understood that the term "antibodies" also includes antibody fragments and any fusion protein that comprises an antibody or an antibody fragment. Thus, the present invention also encompasses the separation of fragments of any one of the above mentioned antibodies as well as fusion proteins comprising such antibodies. In one embodiment, the antibodies are monoclonal antibodies. In a specific embodiment, the antibodies are humanised antibodies. The compounds to be removed from the antibody by the separation or purification can be non product-related material such as HCP, DNA, viruses, leached proteinaceous ligands, cell culture media components, antibiotics etc or they can be product-related material such as aggregated antibodies, misfolded antibodies, antibody fragments, antibody isoforms etc. Removal of product-related material is generally considered as more of a challenge due to the structural similarity with the antibody. However, there is a need to remove it, in particular since e.g. aggregated antibodies can be immunogenic.

As appears from the above, in the present method, a substantially pure fraction of non-adsorbed antibodies is recovered. In this context, the term "substantially pure" is understood to mean that substantially all the non-antibody compounds have been removed. Most advantageously, at least about 80%, such as at least about 95%, i.e. in the interval of 95-100%, such as at least about 98%, i.e. in the interval of 98-100% and preferably at least about 99%, i.e. in the interval of 99-100%, of the total amount of contaminants is removed on the present separation matrix. However, as the skilled person in this field will appreciate, the purity obtained will depend on the concentration of antibody and/or contaminants in the liquid sample applied to the separation matrix as well as other conditions used. Thus, in one embodiment, the antibodies separated according to the present method are antibodies of therapeutic grade. Thus, the antibodies purified according to the invention are useful in research and also for the preparation of antibody pharmaceuticals, such as MAb drugs. An alternative use of the purified antibodies is for diagnostic use. Further, the purified antibodies are also useful in food products such as food additives for humans. For example, bovine antibodies purified according to the present invention are useful in food products.

In a fourth aspect the invention discloses a method of synthesizing a separation matrix, comprising the steps of:
 a) providing a secondary amine $R_5$—NH—$CH_3$ as a start compound, wherein $R_5$ comprises a hydroxyethyl group, a hydroxypropyl group or a five- or six-membered substituted or non-substituted ring structure;
 b) reacting the start compound with an electrophilic reagent $R_4$—X, to form a tertiary amine $R_5$—N($CH_3$)—$R_4$, wherein $R_4$ comprises a five- or six-membered substituted or non-substituted ring structure;
 c) optionally purifying the tertiary amine; and
 d) immobilizing the tertiary amine via the amine group on a support to form a separation matrix.

This method allows the synthesis of a large variety of separation matrices with multimodal anion exchange ligands suitable for different separations of biomolecules. The matrices comprise a quaternary ammonium functionality which allows for ionic interactions and they further comprise one or two ring structures, which provide additional interactions, in particular hydrophobic interactions, while maintaining a compact ligand structure. The methyl group on the nitrogen is small enough to allow steric access to the nitrogen during coupling and also allows a suitable degree of access to the nitrogen during use. A multitude of secondary amines $R_5$—NH—$CH_3$ can be used, in particular commercially available materials such as e.g. 2-(methylamino)ethanol and N-benzyl-methylamine. The electrophilic reagent $R_4$—X can e.g. be a halide such as benzyl chloride or an aldehyde $R'_4$—CHO as described below. In the halide case, step b) can be a single reaction step, while in the aldehyde case, step b) may involve two sequential substeps of Schiff base formation and reduction as outlined below. The purification can e.g. be achieved by extraction, flash chromatography, ion exchange or other well-known methods. One purpose of the purification can be to remove any residual secondary amine or other nucleophilic impurities that may be coupled on the support along with the desired ligand.

In certain embodiments the reagent $R_4$—X is an aldehyde $R'_4$—CHO, wherein $R'_4$ is a five- or six-membered substituted or non-substituted ring structure and step b) comprises reacting the start compound with $R_4$—CHO to form a Schiff base and reducing the Schiff base to form a tertiary amine $R_5$—N($CH_3$)—$CH_2$—$R'_4$. A multitude of aldehydes $R'_4$—CHO are also available and can easily be reacted with either of the amines to produce the corresponding Schiff bases. The reduction can then be performed e.g. by using sodium triacetoxyborohydride or another suitable reduction agent known in the art, such as e.g. $NaBH_4$ or $NaBH_3CN$.

In some embodiments the start compound is 2-(methylamino)ethanol or N-benzyl-methylamine, which are commercially available and are useful as raw materials for creating diverse libraries of multimodal anion exchange ligands.

In some embodiments, 2-(methylamino)ethanol is reacted with p-trifluoromethyl benzaldehyde or cyclohexanealdehyde to form ligands defined by formulas (II) and (III) respectively. In some embodiments, N-benzyl-methylamine is reacted with 3,4,5-trimethoxybenzaldehyde or thiophene-2-carboxaldehyde to form ligands defined by formulas (IV) and (V) respectively.

In certain embodiments, step d) further comprises immobilizing the synthesized separation ligand species via the amine group on a support to form a separation matrix. Suitable immobilization methods have been discussed above. Step d) can also in some embodiments comprise contacting the separation matrix with a mobile phase comprising a protein, e.g. an antibody, and one or more other compounds and measuring the extent of binding of said protein and one or more other compounds to the matrix. The measured data can then be used to select suitable matrices for separation of specific proteins or antibodies from particular mobile phases.

In some embodiments the method further comprises, after step d), a step of:

e) repeating steps a)-d) with a new combination of start compound and electrophilic reagent $R_4$—X, e.g. aldehyde $R'_4$—CHO. This creates a library of or separation matrices which is useful in the selection of suitable matrices for particular separation problems.

In certain embodiments step e) is repeated at least five times, such as at least ten times.

EXAMPLES

Example 1

Ligand Syntheses 2-(methylamino)ethanol and N-benzylmethyl amine are readily available and these amines can be reacted under reductive amination conditions with different aldehydes to get corresponding tertiary amines. From the different reagents available for reductive amination like $NaBH_4$, $NaBH_3CN$ and $NaBH(OAc)_3$, we chose $NaBH(OAc)_3$ as NaBH4 reduces aldehyde and ketones which gives byproducts, NaBH3CN is highly toxic and produces toxic products such as HCN and NaCN upon workup and there is a possibility of contamination of product with cyanide. $NaBH(OAc)_3$ is a mild reagent that exhibits remarkable selectivity as a reducing agent. Aldehydes and ketones are less likely reduced by NaBH(OAc)3. The reductive amination scheme is depicted in FIG. 1. Ac here denotes an acetyl group.

Figure 2:
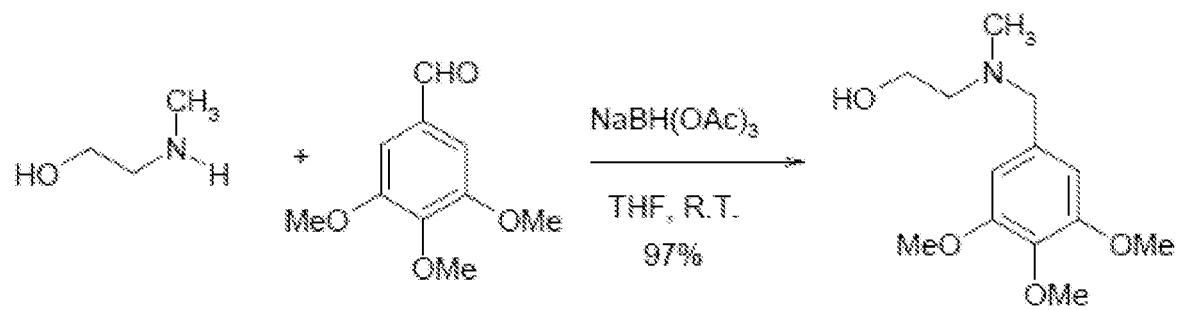
FIG. 2 Example of a ligand synthesis.

FIG. 2 shows the exemplary reaction of 2-(methylamino)ethanol with 3,4,5-trimethoxybenzaldehyde in the presence of sodium triacetoxyborohydride in THF as a solvent. Work up of the reaction provided the desired product (14.2) in 97% yield. This reaction was extended to other aldehydes to produce the corresponding exemplary tertiary amines according to Table 1.

TABLE 1

| Product No. | Amine | Aldehyde | Method | Time (h) | Product | Yield* (%) |
|---|---|---|---|---|---|---|
| 14.2 | 2-(Methylamino)ethanol | 3,4,5-trimethoxy-Benzaldehyde | B | Overnight | 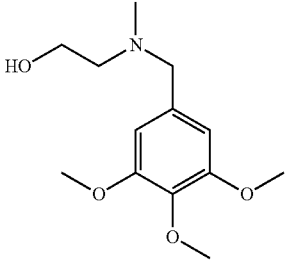 [SMILES: COc1cc(CN(C)CCO)cc(OC)c1OC] | 97 |
| 14.3 | 2-(Methylamino)ethanol | Cyclohexane-carboxaldehyde | A | Overnight | 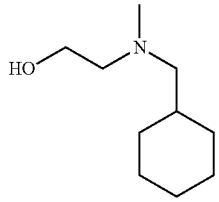 | 95 |
| 14.4 | 2-(Methylamino)ethanol | 2-Thiophene-carboxaldehyde | B | Overnight | 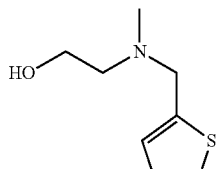 | 90 |
| 14.5 | 2-(Methylamino)ethanol | 2-Furaldehyde | B | 5 | 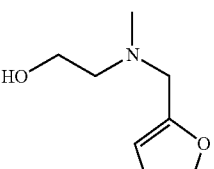 | 87 |

TABLE 1-continued
| | | | | | | |
|---|---|---|---|---|---|---|
| 14.6 | 2-(Methylamino)ethanol | Butyraldehyde | A | Overnight | 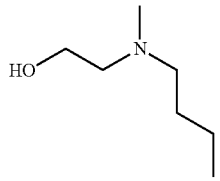 | 67 |
| 14.7 | 2-(Methylamino)ethanol | 3-Pyridine-carboxaldehyde | A | Overnight | 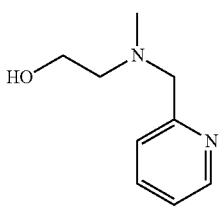 | 60 |
| 14.8 | 2-(Methylamino)ethanol | 4-trifluoroMethyl-benzaldehyde | C | Overnight | 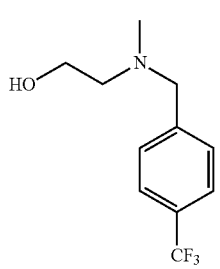 [SMILES: CN(CCO)Cc1ccc(C(F)(F)F)cc1] | 90 |
| 14.9 | 2-(Methylamino)ethanol | 4-acetamido-benzaldehyde | A | Overnight | 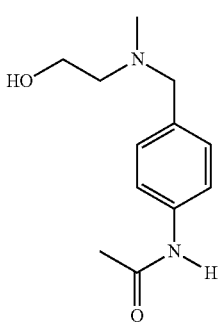 [SMILES: CC(=O)Nc1ccc(CN(C)CCO)cc1] | 60 |
| 14.10 | 2-(Methylamino)ethanol | 1-Naphthaldehyde | A | Overnight | 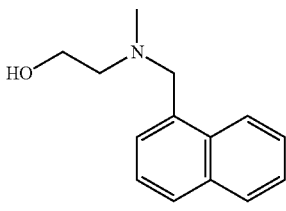 | 64 |
| 14.11 | 2-(Methylamino)ethanol | 4-(Methylsulfonamido)-benzaldehyde | A | 6 | 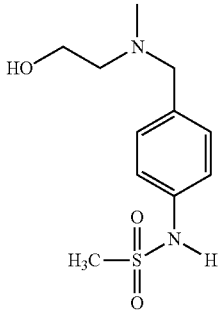 [SMILES: CN(CCO)Cc1ccc(NS(C)(=O)=O)cc1] | 70 |

TABLE 1-continued

| | | | | | | Yield (%) |
|---|---|---|---|---|---|---|
| 14.12 | 2-(Methylamino)ethanol | Pentafluoro-bezaldehyde | A | 2 | HO-CH2CH2-N(CH3)-CH2-C6F5 | 63 |
| 14.13 | N-benzyl-methylamine | Cyclohexane-carboxaldehyde | B | Overnight | Ph-CH2-N(CH3)-CH2-cyclohexyl | 88 |
| 14.15 | N-benzyl-methylamine | 2-Thiophene-carboxaldehyde | B | Overnight | Ph-CH2-N(CH3)-CH2-(2-thienyl) | 96 |
| 14.16 | N-benzyl-methylamine | 2-Furaldehyde | B | Overnight | Ph-CH2-N(CH3)-CH2-(2-furyl) | 84 |
| 14.17 | N-benzyl-methylamine | Butyraldehyde | A | Overnight | Ph-CH2-N(CH3)-CH2CH2CH2CH3 | Quant. |
| 14.18 | N-benzyl-methylamine | Pentafluoro-bezaldehdye | B | 2 | Ph-CH2-N(CH3)-CH2-C6F5 | 69 |
| 14.19 | N-benzyl-methylamine | 3,4,5-trimethoxy-benzaldehyde | B | Overnight | Ph-CH2-N(CH3)-CH2-(3,4,5-trimethoxyphenyl) | 60 |

TABLE 1-continued

| 14.20 | N-benzyl-methylamine | CH₃OCH₂CH₂O—CH₂CH₂OCH₂CHO | B | 3 | 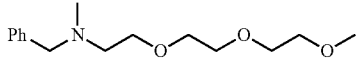 [SMILES: COCCOCCOCCN(C)Cc1ccccc1] | 90 |
| 14.21 | N-Methyl-furfurylamine | CH₃OCH₂CH₂O—CH₂CH₂OCH₂CHO | A | Overnight | 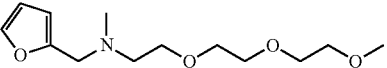 [SMILES: COCCOCCOCCN(C)Cc1ccco1] | 73 |

| Product No. | Amine | Aldehyde | Method | Time | Product | Yield |
| --- | --- | --- | --- | --- | --- | --- |
| 14.22 | N-benzyl-methylamine | 4-triflurormethyl-benzaldehyde | C | Overnight | 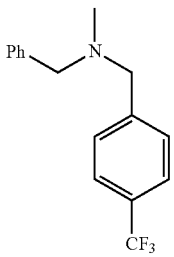 | 90 |
| 14.23 | N-benzyl-methylamine | 3-Pyridine-carboxaldehyde | A | Overnight | 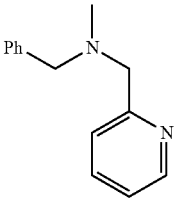 | 85 |
| 14.24 | N-benzyl-methylamine | (DL) glyceraldehyde | C | 5 | 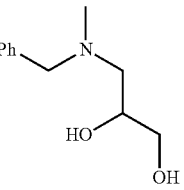 | 50 |

Methods:

A: A mixture of amine (1 mol eq.), aldehyde (1.2 mol eq.) and sodium triacetoxyborohydride (STAB)(1.5-1.6 mol eq.) in THF was stirred at room temperature for time given in the table 1. The reaction mixture was quenched with 1M NaOH (saturated with NaCl) till pH 10-11. The reaction mixture was extracted with ethyl acetate (6×100 mL). The ethyl acetate layer was dried and evaporated. The crude product was purified by silica gel chromatography.

B: The reaction was done as Method A. The ethyl acetate layer from method A was treated with 1M HCl (3×20 mL). The layers were separated and aqueous layer was cooled and neutralized with 1M NaOH (saturated with NaCl). The product obtained was extracted with ethyl acetate (6×100 mL). Ethyl acetate layer was dried and evaporated. The crude product was purified by silica gel chromatography.

C: Same as method A with addition of AcOH (1-2 mol equivalents) in the reaction mixture.

For products 14.2 to 14.12, during workup the aqueous layer was additionally saturated with solid NaCl to get better yields.

2-(N-(Cyclohexylmethyl)-N-methylamino)ethanol (14.3): A mixture of 2-(methylamino)ethanol (1.25 g, 16.64 mmol), cyclohexanealdehyde (2.24 g, 19.97 mmol) and STAB (5.64 g, 26.62 mmol) in THF (60 mL) was reacted as per method A. Purification by silica gel chromatography using (100:1 ethyl acetate/isopropyl amine as a eluent) provided colorless oil. Yield: 2.72 g (95%), Rf: 0.3 (100:1 ethyl acetate/isopropyl amine). Spectral data: 1H NMR (500 MHz, CDCl3) δ 3.55 (t, J=5.4 Hz, 2H), 2.49 (t, J=5.4 Hz, 2H), 2.21 (s, 3H), 2.17 (d, J=7.2 Hz, 2H), 1.79-1.60 (m, 5H), 1.54-1.40 (m, 1H), 1.30-1.09 (m, 4H), 0.94-0.76 (m, 2H). 13C NMR (126 MHz, CDCl3) δ 64.68, 59.28, 58.22, 42.07, 35.64, 31.58, 26.74, 26.00. FIRMS (ESI, m/z) [M+H]+ Calcd for C10H21NO 172.1695 found 172.1692.

2-(N-(4-(Trifluoromethyl)benzyl)-N-methylamino) ethanol (14.8)

A mixture of 2-(methylamino)ethanol (0.71 g, 9.53 mmol), 4-trifluromethylbenzaldehyde (2.00 g, 11.44 mmol), STAB (3.02 g, 14.29 mmol) and acetic acid (0.55 mL, 9.53 mmol) in THF (40 mL) was reacted as per method C. Purification by silica gel chromatography using (17:17:1 ethyl acetate/heptane/isopropyl amine as a eluent) provided colorless oil. Yield: 2.00 g (90%), Rf: 0.27 (17:17:1 ethyl acetate/heptane/isopropyl amine). Spectral data: 1H NMR (500 MHz, CDCl3) δ 7.59 (d, J=8.1 Hz, 2H), 7.45 (d, J=8.0 Hz, 2H), 3.70-3.62 (m, 4H), 2.64 (t, J=5.5 Hz, 2H), 2.27 (s, 3H). 13C NMR (126 MHz, CDCl3) δ 142.75, 129.47 (q, 2JCF=32.5 Hz), 129.07, 125.26 (q, 3JCF=3.7 Hz), 124.40 (q, 1JCF=273.4 Hz), 61.81, 58.53, 58.45, 41.56. HRMS (ESI, m/z) [M+H]+ Calcd for C11H14F3NO 234.1100 found 234.1099.

N-Benzyl-N-methyl(thiophen-2-yl)methanamine (14.15)

A mixture of N-benzylmethylamine (1.24 g, 10.18 mmol), thiophene-2-carboxaldehyde (1.37 g, 12.21 mmol) and STAB (3.23 g, 15.27 mmol) in THF (35 mL) was reacted as per method B. Purification by silica gel chromatography using (100:1:1, heptane/ethyl acetate/isopropyl amine) provided colorless oil. Yield: 2.12 g (96%), Rf: 0.23 (100:1:1, heptane/ethyl acetate/isopropyl amine). Spectral data: 1H NMR (500 MHz, CDCl3) δ 7.40 (d, J=7.3 Hz, 2H), 7.35 (t, J=7.5 Hz, 2H), 7.30-7.25 (m, 2H), 6.99-6.96 (m, 1H), 6.96 (bs, 1H), 3.79 (s, 2H), 3.57 (s, 2H), 2.28 (s, 3H). 13C NMR (126 MHz, CDCl3) δ 142.83, 138.97, 128.87, 128.22, 126.97, 126.32, 125.60, 124.82, 61.06, 56.02, 42.10. FIRMS (ESI, m/z) [M+H]+ Calcd for C13H15NS 218.0998 found 218.0996.

N-Benzyl(3,4,5-trimethoxyphenyl)-N-methylmethanamine (14.19)

A mixture of N-benzylmethylamine (0.89 g, 7.35 mmol), 3,4,5-trimethoxybenzaldehyde (1.74 g, 8.82 mmol) and STAB (2.33 g, 10.99 mmol) in THF (30 mL) was reacted as per method B. Purification by silica gel chromatography using (50:1.5:1, heptane/ethyl acetate/isopropyl amine) provided colorless oil. Yield: 1.2 g (60%), Rf: 0.21 (50:1.5:1, heptane/ethyl acetate/isopropyl amine). Spectral data: 1H NMR (500 MHz, CDCl3) δ 7.38-7.29 (m, 5H), 6.62 (s, 2H), 3.87 (s, 6H), 3.84 (s, 3H), 3.51 (s, 2H), 3.47 (s, 2H), 2.22 (s, 3H). 13C NMR (126 MHz, CDCl3) δ 153.07, 139.15, 136.73, 134.96, 128.85, 128.20, 126.94, 105.49, 62.16, 61.61, 60.82, 56.05, 42.41. HRMS (ESI, m/z) [M+H]+ Calcd for C18H23NO3 302.1750 found 302.1751.

Example 2

Immobilization of Ligands

Base matrix: High rigidity crosslinked agarose beads prepared according to the method described in U.S. Pat. No. 6,602,990. The average bead diameter was 80 μm and the porosity as determined by inverse size exclusion chromatography with dextrans as probe molecules corresponded to a $K_D$ value of 0.54 for dextran of molecular weight 110 kDa, meaning that 54% of the bead volume was available to the dextran molecules. The method for porosity determination is described in L Hagel et al: J Chromatogr A 743, 33-42 (1996).

Allylation: 250 g of the agarose beads (250 mL of drained gel), washed 5× with distilled water, was dried down to 210 g by vacuum suction through the gel in a glass filter funnel and then placed into a 1 L round flask. To the flask was then added 50% NaOH (340 mL) and 1 g of sodium borohydride. The flask was immersed into a water bath at 50° C. and stirring was applied. After 30 min 68 mL of allyl glycidyl ether (AGE) was added. Reaction then progressed for 16.5 hours. The gel was washed with distilled water (3×GV), ethanol (3×GV) and finally distilled water (8×GV).

Figure 3:
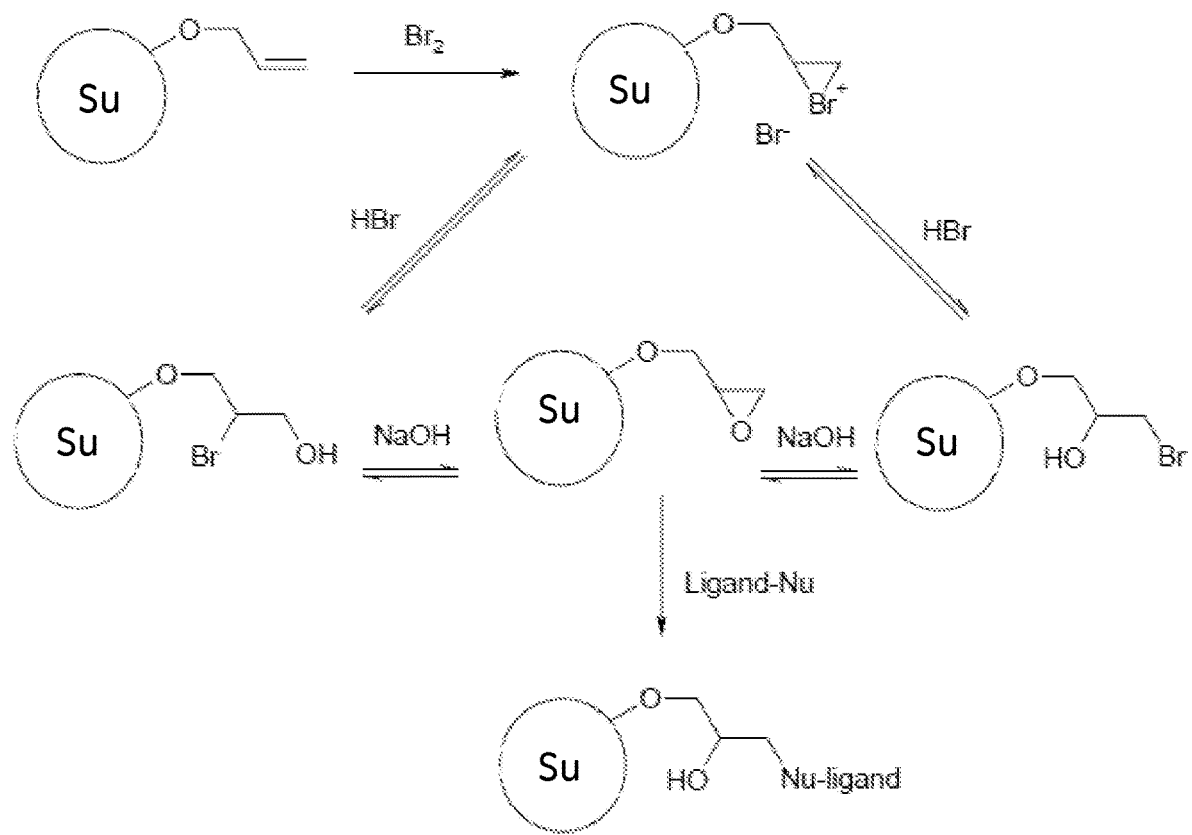
FIG. 3 Example of the coupling of ligands to a support (Su), in this case by bromination of allyl groups on the support.

Immobilization: In order to couple a ligand with a nucleophile group to an allylated gel, the allyl group has to be activated. Activation was done (FIG. 3) by reacting allylated gel beads (the beads are denoted Su in FIG. 3) with Br2 in water, which leads to formation of bromonium groups on the gel and bromine ion in the solution. The bromonium ion on reaction with HBr forms bromohydrins which in turn are converted to an epoxide after treatment with NaOH. Finally this epoxide reacts with the nucleophilic ligand to get the immobilized gel.

The separation matrices with immobilized ligands are listed in Table 2. This table also lists the octanol-water distribution coefficient for each ligand before immobilization, as estimated from the structures by the software ACD/Labs Log P DB v. 9.0. Further, the table lists the ionic capacity (IC) of the matrix prototypes, as determined by chloride capacity titration with silver nitrate. Where multiple IC values are listed for a given ligand, more than one prototype with different ligand content were prepared by primarily varying the allyl content, but in some cases also the ligand concentration or the immobilization temperature.

| Ligand structure | Ligand no. | Mw | pKa | lgP | Allyl level (μmol/ml) | Ligand density (μmol/ml) |
|---|---|---|---|---|---|---|
| (structure: HO-CH2CH2-N(CH3)-CH2-(3,4,5-trimethoxyphenyl)) | 14.2 | 255.3 | 7.50 | 1.17 | 219 | 70 |
| | | | | | 146 | 48 |
| | | | | | 304 | 83 |
| | | | | | 304 | 91 |
| | | | | | 304 | 85 |
| | | | | | 304 | 93 |
| (structure: HO-CH2CH2-N(CH3)-CH2-cyclohexyl) | 14.3 | 171.3 | 8.88 | 2.26 | 219 | 55 |
| | | | | | 304 | 69 |

-continued
| Ligand structure | Ligand no. | Mw | pKa | lgP | Allyl level (μmol/ml) | Ligand density (μmol/ml) |
|---|---|---|---|---|---|---|
| 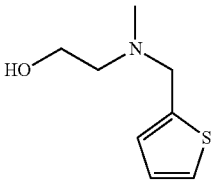 | 14.4 | 171.3 | 7.37 | 1.40 | 219<br>146 | 105<br>64 |
| 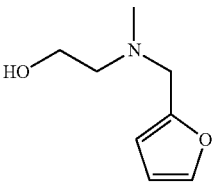 | 14.5 | 155.2 | 7.53 | 0.89 | 219<br>146 | 102<br>69 |
| 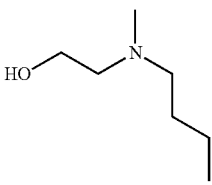 | 14.6 | 131.2 | 8.96 | 1.27 | 219<br>146 | 99<br>63 |
| 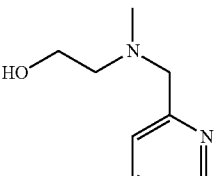 | 14.7 | 166.2 | 7.14 | 0.23 | 219<br>146 | 109<br>82 |
| 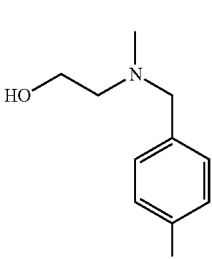 | 14.8 | 179.3 | 7.40 | 2.30 | 305 | 63 |
| 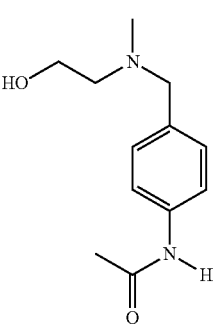 | 14.9 | 222.3 | 7.95 | 0.59 | 219<br>146 | 87<br>53 |

-continued
| Ligand structure | Ligand no. | Mw | pKa | lgP | Allyl level (μmol/ml) | Ligand density (μmol/ml) |
|---|---|---|---|---|---|---|
| 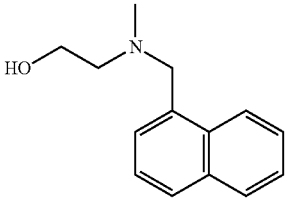 [SMILES: CN(CCO)Cc1cccc2ccccc12] | 14.10 | 215.3 | 7.77 | 2.96 | 305 | 65 |
| 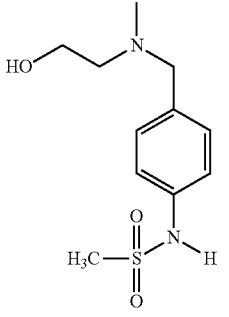 | 14.11 | 258.3 | 7.85 | 0.46 | 219<br>304 | 51<br>70 |
| 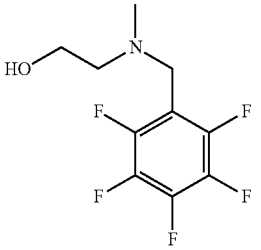 [SMILES: CN(CCO)Cc1c(F)c(F)c(F)c(F)c1F] | 14.12 | 255.2 | 6.42 | 1.91 | 219<br>305 | 23<br>25 |
| 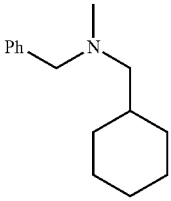 | 14.13 | 217.4 | 8.80 | 4.57 | 219<br>305 | 0<br>8 |
| 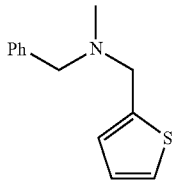 | 14.15 | 217.3 | 7.29 | 3.53 | 305 | 25 |
| 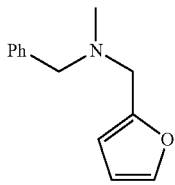 | 14.16 | 201.3 | 7.45 | 3.01 | 305 | 57 |

-continued

| Ligand structure | Ligand no. | Mw | pKa | lgP | Allyl level (μmol/ml) | Ligand density (μmol/ml) |
|---|---|---|---|---|---|---|
| Ph–N(CH₃)–CH₂–C₆F₅ (pentafluorobenzyl) | 14.18 | 301.3 | 6.34 | 4.03 | 219<br>305 | 0<br>0 |
| Ph–N(CH₃)–CH₂–(3,4,5-trimethoxyphenyl) | 14.19 | 301.4 | 7.42 | 3.29 | 305 | 25 |
| Ph–N(CH₃)–CH₂CH₂–O–CH₂CH₂–O–CH₂CH₂–O–CH₃ | 14.20 | 267.4 | 7.85 | 0.45 | 219<br>304 | 60<br>75 |
| Furfuryl–N(CH₃)–CH₂CH₂–O–CH₂CH₂–O–CH₂CH₂–O–CH₃ | 14.21 | 257.3 | 7.46 | −0.39 | 219<br>304 | 75<br>93 |
| Ph–N(CH₃)–CH₂–(4-CF₃-phenyl) | 14.22 | 225.3 | 7.33 | 4.42 | 305 | 63 |
| Ph–N(CH₃)–CH₂–(2-pyridyl) | 14.23 | 212.3 | 7.06 | 2.36 | 305 | 54 |
| Ph–N(CH₃)–CH₂–CH(OH)–CH₂OH | 14.24 | 195.3 | 7.80 | 0.96 | 219<br>304 | 76<br>98 |

Example 3

Evaluation of Separation Matrix Prototypes

Sample preparation: The sample was a mAb feed obtained after the first step of Protein A purification. First the sample was filtered with a 0.2 μm filter. This was followed by a buffer exchange into 2.5 mM Phosphate buffer, pH 7.0, with a HiPrep™ Desalting column. The runs were performed with an ÄKTA Explorer™ 100 chromatography system (GE Healthcare, Sweden). For all the experiments the sample was concentrated to the required concentration by using Centricon filters with a molecular weight cut off of 30 kDa.

Buffer preparation: The buffers for the plate experiments were prepared using an automated Freedom Evo™ Tecan Freedom EVO-2 200 robotic system.

Plate preparation: In the initial screening phase 96-well PreDictor™ filter plates (GE Healthcare, Sweden) were filled with the different prototype media with each well containing 6 μl of the media. The plates were filled using a Gibson robotic system which is programmed to take 300 μl of the media from a 2% slurry, which constitutes 6 μl of media in each well.
1) The plates were tilted upside down a couple of times, with care taken so that the media did not leak out.
2) The top and bottom seals were removed gently and the storage solution which is 20% ethanol was removed using vacuum.
3) The bottom of the plate was wiped to remove traces of the storage solution.

Equilibration
1) Each of the 96 wells were filled with 200 μl of the respective buffer and kept in a shaker for 2 minutes at 1100 rpm.
2) The buffer was removed with vacuum.
3) Steps 1 and 2 were repeated twice.
4) The first step was repeated again but the buffer was removed by centrifugation at 500*g for 1 minute.
5) The buffers and the volume were the same in all the experiments. The buffers were double concentrated since the sample had to be diluted in these buffers.

Loading and Collection of the Sample
1) 200 μl of the sample was added to each of the wells. Since the sample was double concentrated after the buffer exchange, it was diluted with double concentrated buffer.
2) Once the samples were loaded in all the 96 wells, the PreDictor plates were covered with a foil and incubated in a shaker at 1100 rpm for 60 minutes.
3) The flowthrough was collected in a collection plate by centrifugation at 500*g for 1 minute.

Removal of Loosely Bound Protein
1) To fully recover the remaining target protein one or two washes (2*200 μl) were performed with the equilibration buffer.
2) The washes were collected by centrifugation at 500*g for 1 minute in a collection plate.

Screening for the optimum conditions: For this study 20 different prototypes were analysed with some prototypes done with different ligand densities. The mAb sample was buffer exchanged after which the final concentration of the mAb sample was around 5 g/l. For all the experiments two buffer systems, 25 mM Citrate and 50 mM Phosphate were used with three pH's for each of the buffer systems. The pH of the 25 mM Citrate varied from 4.6 to 6.0 and the pH of the 50 mM Phosphate varied from 6.0 to 7.4. The Sodium Chloride (NaCl) concentration was varied from 0 mM to 350 mM. Each experimental condition was replicated once. In each PreDictor™ plate two different prototype media were filled, with one on each half of the plate.

The concentration of the mAb sample after buffer exchanging into 2.5 mM Phosphate was determined by measuring the absorbance at 280 nm using an UV spectrophotometer. The extinction coefficient of the mAb is 1.50. The concentration of the mAb sample to be loaded into the plates was around 5 g/l.

Analysis by Size Exclusion Chromatography: All the analyses in this study were run in an ÄKTA™ Explorer 10 system to which two interconnected Superdex 200 5/150 GL columns were connected. For each analysis 10 μl of the sample was loaded into the columns and Phosphate buffered saline (PBS) was used as mobile phase with a flow rate of 0.35 ml/min for 15 minutes.

From the data obtained with the Size Exclusion chromatography (SEC) analysis, the capacities (Q) for both the monomer and aggregates for each experimental condition were calculated using Equation 1.

$$Q = (C_{ini} - C_{FT})\frac{V_{Sample}}{V_{Medium}} \quad \text{Equation 1}$$

Q is either the monomer capacity ($Q_m$) or the aggregate capacity ($Q_a$), $C_{ini}$ is the initial concentration, $C_{FT}$ is the concentration of the flow through of either the monomer or the aggregate. $V_{Sample}$ denotes the volume of the sample added to each well in the PreDictor™ plate and $V_{Medium}$ is the volume of the medium in each well.

Column prediction: The results from the SEC analysis were used to predict the column behaviour. The yield and purity were calculated for varying loads for each of the prototype media to check for certain experimental conditions that give the desired yield (Equation 2) and purity (Equation 3).

$$\text{Yield} = \frac{V_{load} * C_{ini,m} - CV * Q_m}{V_{load} * C_{ini,m}} \quad \text{Equation 2}$$

$$\text{Purity} = \frac{V_{load} * C_{ini,m} - CV * Q_m}{V_{load} * (C_{ini,m} + C_{ini,a}) - CV * (Q_m + Q_a)} \quad \text{Equation 3}$$

Q from Equation 1 signifies either the monomer or the aggregate capacity at the given experimental condition, $V_{load}$ is the load in ml, $C_{ini}$ is either the initial monomer or aggregate concentration and CV is the column volume.

Automatic data evaluation and column prediction: Automatic integration of monomer and aggregate peaks for all the experimental conditions from the PreDictor™ plates were carried out with the help of a Microsoft Excel macro. The macro enabled a convenient and faster analysis of the huge volume of data for the different conditions. The predictions were then performed using built-in functions in Microsoft Excel.

Host Cell Protein (HCP) Analyses: HCP levels were measured with commercial anti-CHO antibodies using Gyrolab Bioaffy 20 HC microlaboratory discs. The experiments were performed in an automated immunoassay instrument called Gyrolab™ workstation LIF (Gyros AB, Sweden).

Results: A typical two-step process is based on Mab Select Sure™, a Protein A derived media, as the initial capture step and Capto™ adhere as the second step for aggregate removal and HCP reduction. Here we investigate the different multimodal ligands as an alternative to Capto™ adhere and study their effects on aggregate removal and HCP reduction. For these studies a monoclonal antibody feed containing approximately 15% of aggregates, was used as the sample for the second step for all the prototype media. Screening and optimization of the process conditions were performed with the goal of obtaining less than 1% aggregates with acceptable yields and with considerable reduction of HCP levels in the final product.

Screening for initial conditions with PreDictor™ plates: One of the goals of the initial screening phase was to determine the optimal experimental condition for each of the prototype media in a parallelized format.

Flowthrough experiments with PreDictor™ plates: An IgG sample containing ~15% aggregates was used. After loading the sample onto the PreDictor™ plates, the flowthrough fractions were collected along with the washes and subjected to SEC analysis. The results from the SEC analysis were used to calculate the capacities (Q) (Equation 1). To calculate the estimated column yield and purity from the plate data, equations 2 and 3 were used.

These column predictions for yield and purity were performed with all the prototypes for the best conditions. The predictions for yield and purity were calculated for different loads using Microsoft Excel™.

The predictions for the prototypes at high purity and different yields, along with different conditions, are shown in Table 1.

TABLE 1

Column predictions for yield and purity for all the prototypes.

| Ligand | Ligand content (μmol/ml) | Buffer | pH | Salt (mM) | Purity (%) | Yield (%) | Load (g/l) |
|---|---|---|---|---|---|---|---|
| 4-ABA* | 54 | Citrate | 4.6 | 0 | 98.9 | 96.7 | 60.2 |
| 14.8 | 63 | Citrate | 4.6 | 233 | 99 | 96.6 | 69.1 |
| 14.23 | 54 | Citrate | 5.3 | 0 | 98.8 | 95.9 | 80.5 |
| 14.15 | 25 | Citrate | 4.6 | 117 | 98.9 | 94.8 | 79.6 |
| 14.3 | 69 | Citrate | 6 | 117 | 99.4 | 94.6 | 31.4 |
| 14.7 | 109 | Citrate | 5.3 | 350 | 99.1 | 94.6 | 20.6 |
| 14.12 | 25 | Citrate | 5.3 | 0 | 99.1 | 94.1 | 46.8 |
| 14.17 | 67 | Citrate | 5.3 | 117 | 98.7 | 93.9 | 76.8 |
| 14.19 | 25 | Citrate | 4.6 | 0 | 99 | 92.9 | 76 |
| 14.16 | 57 | Citrate | 4.6 | 0 | 98.8 | 87.2 | |
| 14.21 | 75 | Citrate | 5.3 | 0 | 98.8 | 85.4 | |
| 14.21 | 93 | Citrate | 4.6 | 0 | 98.6 | 79 | |
| 14.10 | 65 | Citrate | 4.6 | 0 | 98.5 | 54.5 | |
| 14.4 | 105 | Citrate | 5.3 | 0 | 99 | 50.4 | 113.7 |
| 14.3 | 55 | Phosphate | 6.7 | 0 | 99.1 | 49 | |
| 14.24 | 75 | Citrate | 5.3 | 0 | 99 | 49 | |
| 14.9 | 53 | Phosphate | 6 | 0 | 98.9 | 49 | |
| 14.5 | 102 | Phosphate | 6 | 0 | 98.9 | 47.9 | |
| 14.9 | 87 | Phosphate | 6 | 0 | 99.2 | 47.5 | |
| 14.5 | 69 | Phosphate | 6.7 | 0 | 99 | 46.6 | |
| 4-ABA* | 74 | Citrate | 5.3 | 0 | 99.1 | 45 | |
| 14.20 | 60 | Phosphate | 7.4 | 0 | 98.8 | 44.9 | |
| 14.2 | 70 | Phosphate | 6 | 0 | 98.9 | 43.7 | |
| 14.4 | 64 | Phosphate | 6.7 | 117 | 98.9 | 43.3 | |
| 4-ABA* | 35 | Citrate | 5.3 | 0 | 98.7 | 41.9 | |
| 14.24 | 98 | Citrate | 4.6 | 0 | 98.8 | 37 | |
| 14.6 | 99 | Phosphate | 6 | 0 | 98.9 | 36.8 | |
| 14.6 | 63 | Phosphate | 6 | 0 | 99 | 33.3 | |
| 14.11 | 51 | Phosphate | 6 | 0 | 98.8 | 32.1 | |
| 14.7 | 82 | Phosphate | 6 | 0 | 99.3 | 25.5 | |
| 14.2 | 85 | Citrate | 5.3 | 0 | 99 | 16.6 | |
| 14.11 | 70 | Phosphate | 6 | 0 | 98.9 | 14.9 | |

*4-ABA is 4-aminobenzylamine

Figure 6:
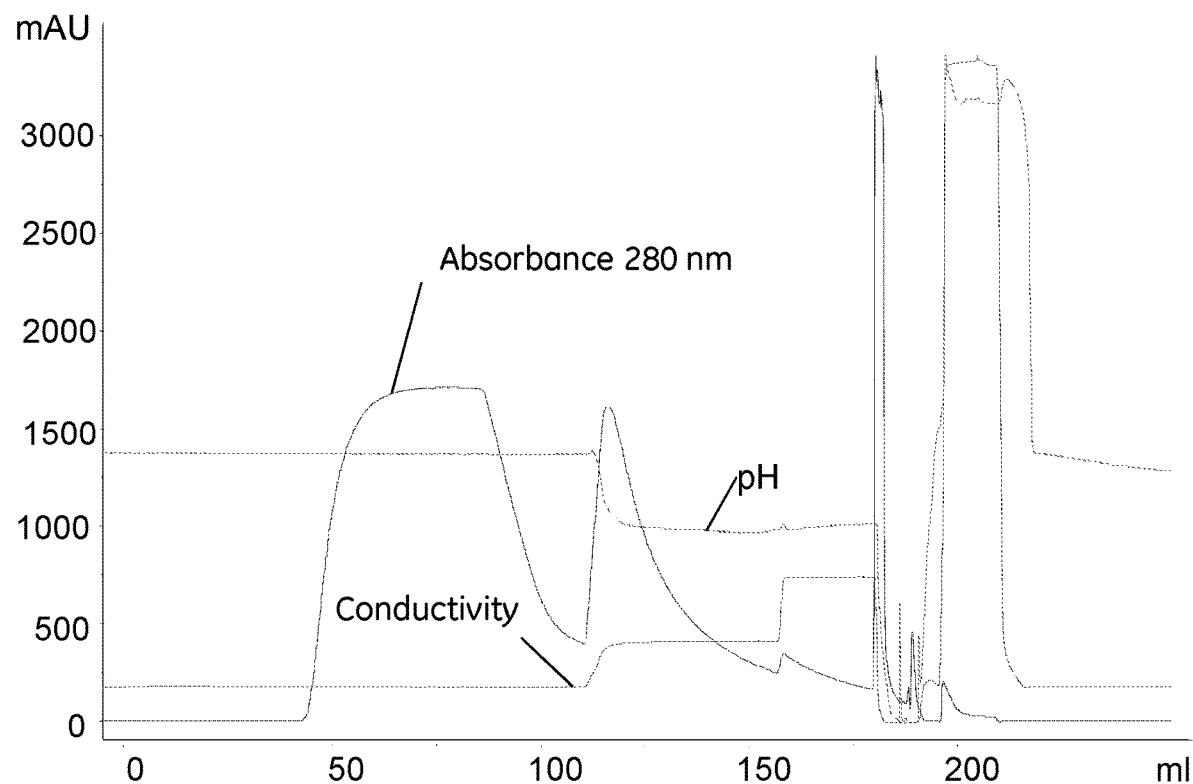
FIG. 6 Chromatographic profile of a comparative matrix with N-methyl, N-benzyl ethanolamine ligands.

In comparison, a prototype on the same base matrix, with 100 μmol/ml N-benzyl-n-methyl ethanolamine coupled via bromination of allylated matrix, at a load of 87 g/l, pH 6.0 with no salt added gave a purity of 99.1% and a yield of 64%. The N-benzyl-N-methylethanolamine ligand has a lgP value of 1.73 and a pKa of 7.93. The chromatogram from this experiment is shown in FIG. 6.

Column Experiments: The prototypes which met the goal of obtaining less than 1% aggregates (~99% monomer purity) with acceptable yields in the predictions were selected to be run in small Tricorn™ columns. Accordingly, 6 different prototype media were selected which met the predefined conditions. The structures of the four best performing prototypes and their properties in comparison with a reference prototype prepared according to the teachings of U.S. Pat. No. 7,867,784 are shown in Table 2.

TABLE 2

The four best prototypes and their properties in comparison with Capto Adhere.

| Ligand Structure | Ligand no. | Sim Log P value | pKa | Ligand density (μmol/ml) |
|---|---|---|---|---|
| (N-benzyl-N-methylethanolamine structure) | Ref | 1.73 | 7.93 | 100 |
| (structure with CF3-benzyl group) | 14.8 | 2.3 | 7.4 | 63 |
| (structure with cyclohexylmethyl group) | 14.3 | 2.26 | 8.88 | 69 |
| (structure with trimethoxybenzyl and Ph-CH2 group) | 14.19 | 3.91 | 7.42 | 25 |

TABLE 2-continued

The four best prototypes and their properties in comparison with Capto Adhere.

| Ligand Structure | Ligand no. | Sim Log P value | pKa | Ligand density (μmol/ml) |
|---|---|---|---|---|
| Ph-CH2-N(CH3)-CH2-thiophene | 14.15 | 3.53 | 7.29 | 25 |

The 6 prototype media were packed into columns and the runs were performed for the best experimental conditions from the PreDictor™ plate experiment which gave the desired yield and purity (Table 3). One important observation made during the column runs was that the protein tends to precipitate in 25 mM Citrate for pH's below six and hence the next best condition in 50 mM Phosphate was chosen for the column runs.

TABLE 3

Column results of selected prototypes.

| Prototypes | Buffer | pH | NaCl concn (mM) | Purity (%) | Yield (%) | Load (g/l) |
|---|---|---|---|---|---|---|
| 14.8 | 50 mM Phosphate | 6 | 233 | 99.5 | 84 | 40 |
| 14.3 | 50 mM Phosphate | 6 | 117 | 99.4 | 80 | 25 |
| 14.19 | 50 mM Phosphate | 6 | 117 | 99.3 | 69 | 45 |
| 14.15 | 50 mM Phosphate | 6 | 0 | 97.5 | 71 | 40 |
| 14.4 | 25 mM Citrate | 5.3 | 0 | 98.7 | 93 | 60 |
| 4-ABA | 25 mM Citrate | 4.6 | 0 | 97.2 | 26 | 50 |

Figure 4:
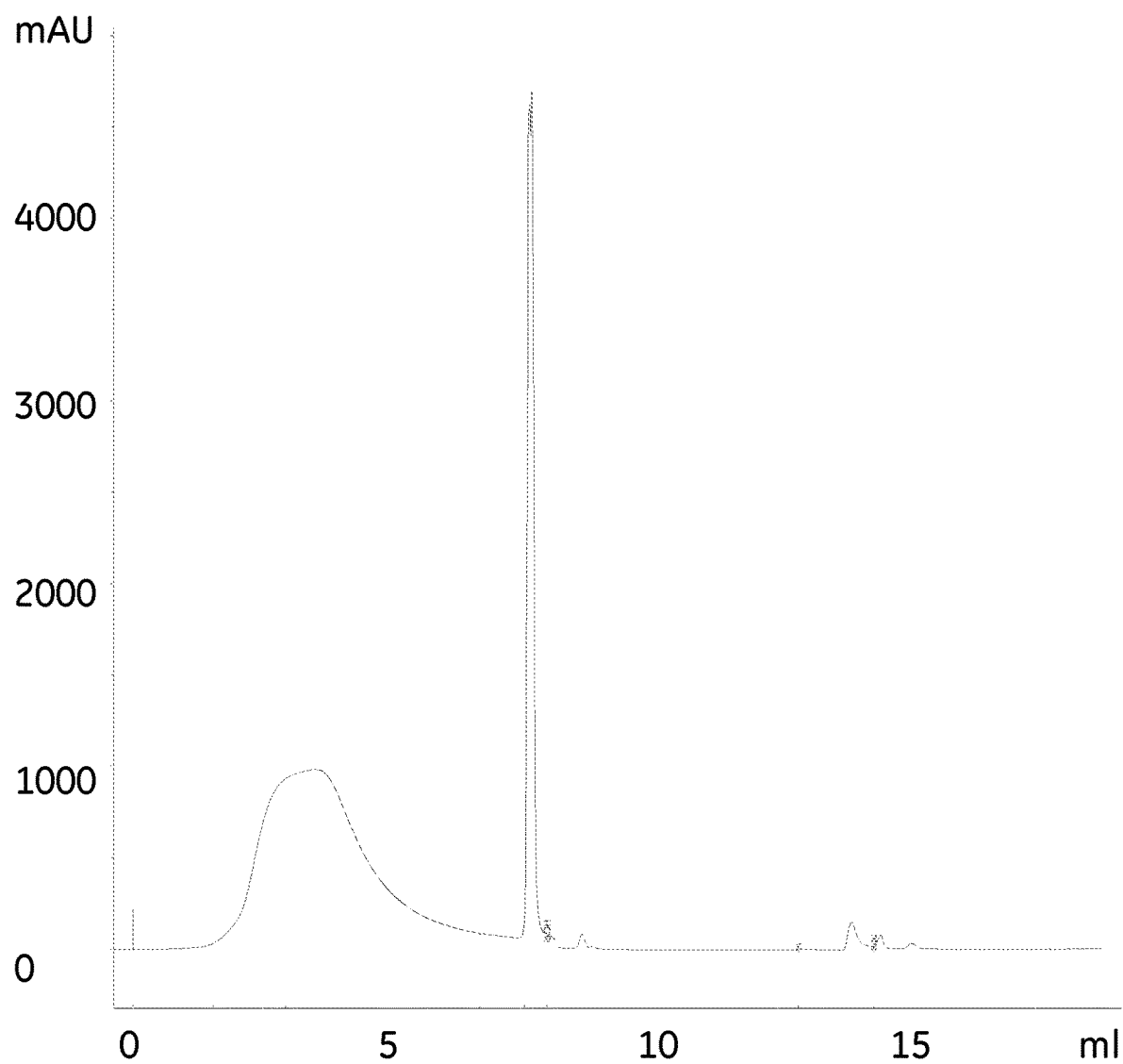
FIG. 4 Chromatographic profile of a prototype matrix according to the invention with conditions selected from the initial screening with the PreDictor™ plates.

The residence time for all the prototypes was 5 minutes. The chromatographic profile of the column runs for one of the promising prototypes is shown in FIG. 4.

Figure 5:
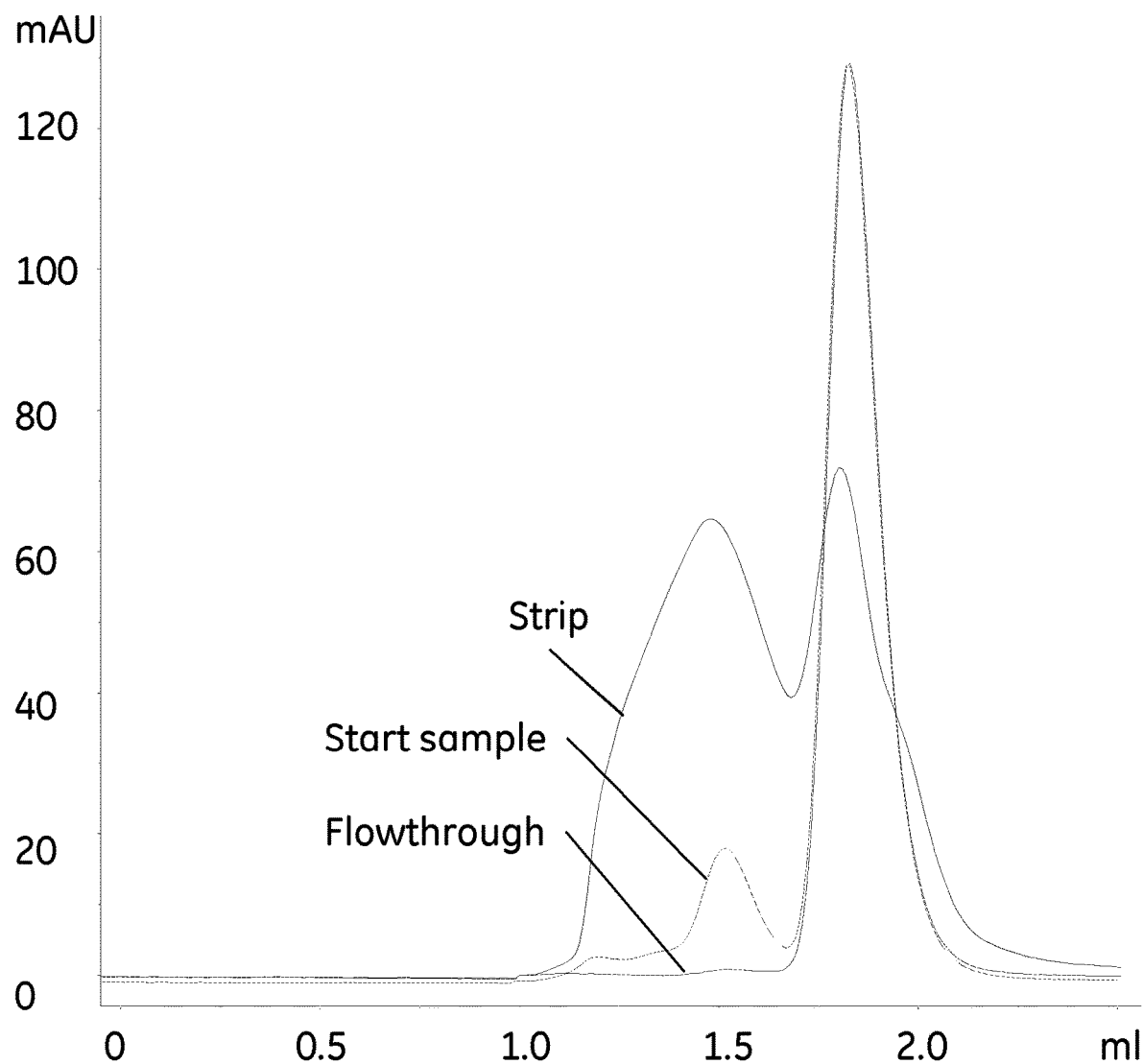
FIG. 5 Overlay plot of the SEC analysis of the start sample, flowthrough and the strip fractions (peak in red represents the start sample, blue peak represents flowthrough, black peak represents the strip fraction). Start sample and flowthrough have been normalized against the monomer peak height.

SEC ANALYSIS RESULTS: The SEC analysis result of one of the prototypes with the chromatographic peaks from the three fractions (start sample, flowthrough and strip) is shown in FIG. 5.

HCP Results from PreDictor™ plate experiments: The HCP content in the flowthrough after the plate experiments was determined for all the prototypes at the conditions given by lower $Q_m/Q_a$ values. Four prototypes showed a considerable reduction in HCP (<400 ppm) despite the large loads done in the plates (approximately 170 mg/ml). From Table 4 it is obvious that low salt concentration has a considerable effect on HCP removal. This is probably attributed to the fact that sodium chloride ions compete with HCP in binding to the ligand. Interestingly, two of the four prototypes performing well in the HCP reduction also were good at aggregate removal.

TABLE 4

HCP level of 4 different prototypes from PreDictor™ plate experiments

| Prototype | Buffer | pH | NaCl concn. (mM) | HCP level ppm (750) |
|---|---|---|---|---|
| 14.8 | 25 mM Citrate | 4.6 | 0 | 325.6 |
| 14.10 | 25 mM Citrate | 4.6 | 0 | 350.2 |
| 14.16 | 25 mM Citrate | 5.3 | 117 | 390 |
| 14.19 | 25 mM Citrate | 4.6 | 0 | 362.3 |
| 14.19 | 25 mM Citrate | 5.3 | 0 | 354.4 |

The HCP results, as can be seen from Table 5, shows a considerable reduction of HCP content in comparison with the high amount of HCP present in the start sample. The buffers for the column experiments were changed to 50 mM Phosphate due to the effects of protein precipitation in citrate buffer and hence these results cannot be directly compared to the HCP results from the PreDictor™ plate experiments. One general trend observed from this data is that at low salt concentrations there is better HCP removal with the exception of the first prototype (14.8) which has a slightly higher NaCl concentration in comparison to others. The performance of the first prototype (14.8) gives sufficient credence for it to be investigated further at low salt concentrations.

TABLE 5

HCP level of 5 prototypes from the column experiments. The start sample contained 881 ppm.

| Prototype | Buffer | pH | NaCl concn. (mM) | Load (g/l) | HCP level (ppm) |
|---|---|---|---|---|---|
| 14.8 | 50 mM Phosphate | 6 | 233 | 40 | 24 |
| 14.3 | 50 mM Phosphate | 6 | 117 | 25 | 37 |
| 14.4 | 25 mM Citrate | 5.3 | 0 | 60 | 39 |
| 14.19 | 50 mM Phosphate | 6 | 117 | 45 | 73 |
| 14.15 | 50 mM Phosphate | 6 | 117 | 60 | 78 |

Thirty-three different types of multimodal ligands were studied using High Throughput Process Development (HTPD) employing the capabilities of the 96 well PreDictor™ plates. The two best prototypes which gave high purity and yield from this study are 14.8 and 14.3, with the structures as shown in Tables 1 and 2.

In general, an increase in hydrophobicity, as observed from the Log P values, up to a certain extent leads to a better aggregate removal at high yields. The reduction of HCP from the column experiments is significant since from an initial HCP level of 881 ppm it has been reduced to 24 ppm for the best performing prototype which is almost 40 times reduction in HCP content. These results are remarkable even though the results between the plate and column experiments are not comparable since the buffers were changed due to the effect of protein precipitation.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A separation matrix comprising a plurality of separation ligands defined by formula (I)

$$R_1\text{-}L_1\text{-}N(R_3)\text{-}L_2\text{-}R_2 \quad (I)$$

immobilized on a support via the amine group of formula (I),
wherein $R_1$ is a hydroxyethyl group or a five- or six-membered, substituted or non-substituted ring structure;
$L_1$ is either a methylene group or a covalent bond;
$R_2$ is a five- or six-membered, substituted or non-substituted ring structure;
$L_2$ is either a methylene group or a covalent bond; and
$R_3$ is a methyl group;
wherein said ligands in free form have an octanol-water distribution coefficient (lg P) of 1.8-5;
wherein if $R_1$ is a hydroxyethyl group, $L_1$ is a covalent bond and $R_2$ is a substituted aromatic ring structure or a substituted or non-substituted aliphatic ring structure; and
wherein the separation ligands are defined by formula (IV) or (V):

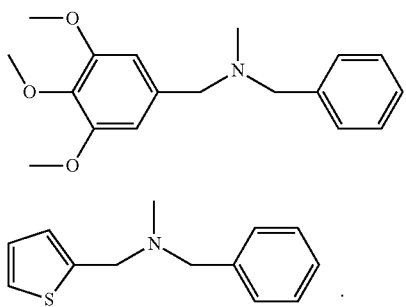

2. The separation matrix according to claim 1, wherein said ligands in free form have an octanol-water distribution coefficient (lg P) of 2-4.

3. The separation matrix according to claim 1, wherein the immobilized separation ligands are immobilized on the support Su via a spacer Sp, as defined in formula (VI)

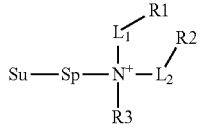

4. The separation matrix according to claim 3, wherein the spacer Sp comprises a chain of 2-8 carbon atoms, optionally at least one of interrupted by and ending in one or more ether groups and optionally substituted by one or more hydroxyl groups.

5. The separation matrix according to claim 1, wherein the support comprises porous particles.

6. The separation matrix according to claim 1, wherein the support comprises a porous membrane.

7. The separation matrix of claim 1, wherein the plurality of separation ligands are defined by formula (IV).

8. The separation matrix of claim 1, wherein the plurality of separation ligands are defined by formula (V).

9. The separation matrix of claim 1, wherein the separation matrix has an antibody yield of at least 90%.

10. A method of separating one or more antibodies from one or more other compounds in a liquid sample, comprising the steps of a) providing a mobile phase comprising said antibodies and other compound(s); and b) contacting said mobile phase with a separation matrix according to claim 1.

11. The method of claim 10, wherein the conductivity of said mobile phase is at least 10 mS/cm.

12. The method of claim 10, wherein said mobile phase comprises an antibody-containing eluate from a previous affinity chromatography step, ion exchange step, multimodal chromatography step, or hydrophobic interaction chromatography step.

13. The method of claim 10, wherein the separation matrix is provided in a chromatography column, the mobile phase is passed through said column by at least one of gravity and pumping, and the antibodies are recovered in the flow-through of the column.

14. The method of claim 10, wherein the separation matrix is provided in a chromatography column, in step b) the mobile phase is passed through said column by at least one of gravity and pumping and at least part of the antibodies adsorb to the column and in a further step c) an elution buffer is passed through the column and antibodies are recovered in the elution buffer after passage through the column.

15. The method of claim 10, wherein in step b) a suspension of matrix particles is contacted with the mobile phase, in a further step c) the matrix particles are separated from the mobile phase by sedimentation, centrifugation or under the influence of a magnetic field and in an optional further step d) the antibodies are recovered in the separated mobile phase.

* * * * *